(12) United States Patent
Crudden et al.

(10) Patent No.: US 7,776,611 B2
(45) Date of Patent: Aug. 17, 2010

(54) OPTICAL SENSOR USING FUNCTIONALIZED COMPOSITE MATERIALS

(75) Inventors: Cathleen M. Crudden, Kingston (CA); Hans-Peter Loock, Kingston (CA); Steven E. Dickson, Dartmouth (CA); Jenny Du, Calgary (CA); Larbi M. S. Benhabib, Brantford (CA); R. Stephen Brown, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 599 days.

(21) Appl. No.: 11/635,816

(22) Filed: Dec. 8, 2006

(65) Prior Publication Data

US 2007/0184557 A1    Aug. 9, 2007

Related U.S. Application Data

(60) Provisional application No. 60/748,197, filed on Dec. 8, 2005.

(51) Int. Cl.
*G01N 21/62* (2006.01)
*G01N 21/00* (2006.01)

(52) U.S. Cl. .................................. 436/171; 436/164

(58) Field of Classification Search ................... 436/171
See application file for complete search history.

(56) References Cited

U.S. PATENT DOCUMENTS

| | | | |
|---|---|---|---|
| 4,568,647 | A | 2/1986 | Sanford |
| 5,279,940 | A | 1/1994 | Kissel |
| 5,864,641 | A | 1/1999 | Murphy et al. |
| 6,417,236 | B1 | 7/2002 | Hobson et al. |
| 6,875,615 | B2 | 4/2005 | Fraga Trillo et al. |
| 7,211,192 | B2 | 5/2007 | Shea et al |
| 2005/0090015 | A1 * | 4/2005 | Hartmann-Thompson ... 436/166 |
| 2006/0258015 | A1 | 11/2006 | Ueno et al. |

FOREIGN PATENT DOCUMENTS

| | | | |
|---|---|---|---|
| EP | 1 251 346 A1 * | 10/2002 | |
| EP | 1416271 A1 | 5/2004 | |
| EP | 1529804 A1 | 5/2005 | |
| WO | WO 03/055452 | 7/2003 | |

OTHER PUBLICATIONS

Tao et al . Mercury atomic absorption by mercury atoms in water observed with a liquid core waveguide as a long path absorption cell, Analyst, 2004, 129, 342-346.*
International Search Report for PCT/CA2006/002001, filed Dec. 8, 2006.
Al-Abadleh, H. A., et al. (2004) "Chromium(VI) Binding to Functionalized Silica/Water Interfaces Studied by Nonlinear Optical Spectroscopy." Journal of the American Chemical Society 126(36): 11126-11127.

Allsop, T., et al., (2001) "Detection of organic aromatic compounds in paraffin by a long-period fiber grating optical sensor with optimized sensitivity." Optics Communications 191(3-6): 181-190.
Bhatia, V., et al., (1996) "Optical fiber long-period grating sensors." Optics Letters 21(9): 692-694.
Bhatia, V., (1999) "Applications of long-period gratings to single and multi-parameter sensing." Optics Express 4(11): 457-466.
Chong, J.H., et al., (2004) "Measurements of refractive index sensitivity using long-period grating refractometer." Optics Communications 229(1-6): 65-69.
Cusano, A., et al. (2005) "High-sensitivity optical chemosensor based on coated long-period gratings for sub-ppm chemical detection in water", Applied Physics Letters, 87, 234105-1-234105-3.
Cusano, A., et al. (2005) "Cladding mode reorganization in high-refractive-index-coated long-period gratings: effects on the refractive-index sensitivity", Optics Letters, 30(19): 2536-2538.
DeLisa, M. P., et al. (2000) "Evanescent wave long-period fiber bragg grating as an immobilized antibody biosensor", Analytical Chemistry, 72(13) 2895-2900.
Del Villar, I., et al. (2005) "Optimization of sensitivity in long period fiber gratings with overlay deposition." Optics Express 13(1): 56-69.
Giordano, M., et al. (2004) "Optical sensor based on ultrathin films of δ-form syndiotactic polystyrene for fast and high resolution detection of chloroform." Applied Physics Letters 85(22): 5349-5351.
Giordano, M., et al. (2005) "Syndiotactic polystyrene thin film as sensitive layer for an optoelectronic chemical sensing device." Sensors and Actuators B-Chemical 109: 177-184.
Lee, S.T., et al. (2003) "Long period gratings in multimode optical fibers: Application in chemical sensing." Optics Communications 224(4-6): 237-241.
Lu, Y. et al. (1996) "Chemical sensors based on hydrophobic porous sol-gel films and ATR-FTIR spectroscopy." Sensors and Actuators B-Chemical 35-36: 517-521.
Pilla, P., et al. (2005) "Optical chemo-sensor based on long period gratings coated with δform syndiotactic polystyrene." IEEE Photonics Technology Letters 17(8): 1713-1715.

(Continued)

*Primary Examiner*—Walter D Griffin
*Assistant Examiner*—Christine T Mui
(74) *Attorney, Agent, or Firm*—Stephen J. Scribner; Carol Miernicki Steeg; Angela Lyon

(57) ABSTRACT

The invention relates to a method for sensing the presence of at least one analyte in a medium, comprising disposing in the medium a functionalized composite material such that the at least one analyte is absorbed by the functionalized composite material, the functionalized composite material having at least one optical property that is modulated by absorption of the at least one analyte; and measuring modulation of the at least one optical property of the functionalized composite material; wherein modulation of the at least one optical property of the functionalized composite material is indicative of the presence of the analyte in the medium. The invention also relates to an optical sensor for sensing the presence of at least one analyte in a medium, and a functionalized composite material having at least one optical property that is modulated upon absorption of one or more analyte.

20 Claims, 7 Drawing Sheets

OTHER PUBLICATIONS

Rees, N.D., et al. (2002) "Optical fiber long-period gratings with Langmuir-Blodgett thin-film overlays." Optics Letters 27(9): 686-688.

Shu, X. et al. (1999) "Highly sensitive chemical sensor based on the measurement of the separation of dual resonant peaks in a 100-μm-period fiber grating." Optics Communications 171: 65-69.

Walcarius, A., et al. (2003) "Grafted silicas in electroanalysis: Amorphous versus ordered mesoporous materials." Electroanalysis 15(5-6): 414-421.

Wang, Z., et al. (2005) "Analysis of optical response of long period fiber gratings to nm-thick thin-film coatings." Optics Express 13(8): 2808-2813.

* cited by examiner

OPTICAL SENSOR USING FUNCTIONALIZED COMPOSITE MATERIALS

RELATED APPLICATIONS

This application claims the benefit of the filing date of U.S. Patent Application No. 60/748,197, filed on Dec. 8, 2005, the contents of which are hereby incorporated by reference in entirety.

FIELD OF THE INVENTION

This invention relates to functionalized composite materials having selective absorption for specific analytes, methods for the preparation of such materials as films, and optical sensors employing such films for optical detection of analytes.

Since the introduction of mesoporous molecular sieves in the 1990's (Beck et al. 1992; Zhao et al. 1998b), the field has expanded to include a variety of functional materials (Gier et al. 1998). Most early work focused on the introduction of functional groups by reacting trialkoxysilyl or trichlorosilyl groups with silanol groups on the surface of pre-formed silicates. Subsequent work showed that functional groups could be incorporated during sol-gel preparation by co-mixing the functional trialkoxysilyl group and the silicate monomer (such as $Si(OEt)_4$) (Wen et al. 1996). Incorporation by this method has the advantage that the functionalized trialkoxysilane group is bound directly to the backbone of the material, which likely renders it more hydrolytically stable, and more evenly distributed throughout the material (Lim et al. 1999). The downside of this method is that the incorporation is limited to approximately 25%, after which point the order of the resulting material suffers. In addition, the functional group being introduced must be robust enough to survive the synthesis conditions for the silicate, which can be harsh (e.g., strong aqueous acid and high temperature).

Another way to incorporate organic functionality into the backbone of the silicate is to employ monomers containing two or more non-hydrolyzable silicon-carbon bonds, such as (1) to (5), below (Baney et al. 1995; Loy et al. 1995).

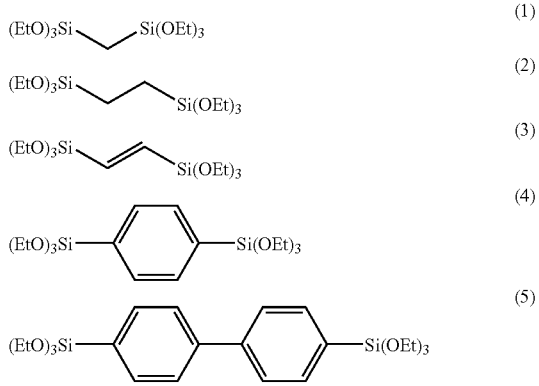

These monomers are well-known for the preparation of regular amorphous silsesquioxanes (Oviatt et al. 1993; Loy et al. 1999). Although the presence of a surfactant template is required to introduce order, significant porosity can be present in some of these organic/inorganic composites. In particular, materials made from phenylene-bridged organic monomers such as (4) have high mesoporosity and surface areas up to 1800 $m^2/g$ (Schaefer et al. 2004).

As previously noted, the pore structure of such composites lacks the order of materials made using a template, but this may not affect function. In some applications, such as uptake of an analyte into a mesoporous film, a disordered structure may have advantages over one in which channels lie parallel to the surface. In addition, these materials can be used directly without removing the surfactant, which is an advantage since calcination of organically-modified films may cause damage to the film (Jung et al. 2004; Grosso et al. 2001).

Silicates functionalized with mercaptopropyl and aminopropyl groups have received considerable attention due to their ability to form complexes with a wide variety of species (Liu et al. 2000). In addition, more complex ligands including isocyanurates (Olkhovyk et al. 2005b; 2005c), benzoylthioureas (Antochshuk et al. 2003; 2004; Olkhovyk et al. 2004; 2005a), calixarenes, dithiocarbonates (Venkatesan et al. 2003), and acetamide phosphonic acids (Yantasee et al. 2005), among others have been employed for the absorption of heavy metals. Functionalized mesoporous silicates have been successfully employed as scavenger materials for several metals including mercury (Feng et al. 1997; Mercier et al. 1997; 1998; Liu et al. 1998a; 1998b; Liu et al. 2000; Schroden et al. 2002; Yoshitake et al. 2002; Antochshuk et al. 2002; 2003; Etienne et al. 2003; Olkhovyk et al. 2004; Aguado et al. 2005; Olkhovyk et al. 2005a-c; Yoshitake 2005), lead (Yantasee et al. 2003; 2004; 2005), copper (Hossain et al. 2002; Yantasee et al. 2004), cadmium (Yantasee et al. 2004), chromium (Yoshitake et al. 2002; Al-Abadleh et al. 2004; Nam et al. 2005), arsenic (Fryxell et al. 1999; Yoshitake et al. 2002), nickel, gold, cobalt (Hanzel et al. 2000; Sayen et al. 2003), palladium (Kang et al. 2003; 2004a; 2004b; Crudden et al. 2005), platinum (Kang et al. 2003; 2004a; 2004b), and radionuclides (Trens et al. 2002). Remarkable selectivity for one metal in the presence of others has been demonstrated in many of the above cases. For example, Walcarius has shown that in the environmentally significant pH range of 4 to 7, mercaptopropyl-modified mesoporous silica selectively absorbs mercury ($1\times10^{-5}$M) in the presence of $1\times10^{-3}$ M solutions of Cu(II), Co(II), Pb(II), Ni(II), Zn(II). This behaviour is attributed to the fact that the silanol groups are primarily protonated in this range and therefore are not good binding sites for metal cations (Walcarius et al. 1999).

In addition, derivatized silicate materials have also been used as adsorbents and sensors for organic hydrocarbons (Moscatelli et al. 2004) including benzene (Lu et al. 1996), and also as sensors for water (Bertolo et al. 2005) or alcohols. Adsorption of gaseous analytes such as carbon dioxide (McCool et al. 2005) or elemental mercury (M et al. 2005) has also been reported.

Far less attention has been paid to the thin film morphology of mesoporous materials compared to the more commonly used powdered form (Lee et al. 2006). This is likely because synthetic techniques for the former are less developed. Thin film requirements tend to pose synthetic challenges, namely the films should be continuous and free of large cracks. Strict control of process parameters during stages such as calcination or drying can help to alleviate this problem; however, mesoporous films are generally limited to thicknesses under 1 micron. Strict control over other factors such as relative humidity and aging temperature are important to control in order to obtain a film with desired pore structure (Lee et al. 2006).

The evaporation-induced self-assembly (EISA) mechanism is the most widely used formation process for mesoporous thin-films, especially with dip coated substrates, and was originally proposed by Brinker and co-workers (Brinker et al. 1999). This process involves evaporation of volatile components from a coated substrate and gradual increase of surfactant template concentration above the critical micelle concentration, which results in surfactant self-assembly. The silica species present can still undergo hydrolysis and condensation to form pore walls of the mesoporous film.

SUMMARY OF THE INVENTION

According to one aspect of the invention there is provided a method for sensing the presence of at least one analyte in a medium, comprising: disposing in the medium a functionalized organic/inorganic composite material such that the at least one analyte is absorbed by the functionalized organic/inorganic composite material, the functionalized. composite material having at least one optical property that is modulated by absorption of the at least one analyte; and measuring modulation of the at least one optical property of the functionalized composite material; wherein modulation of the at least one optical property of the functionalized composite material is indicative of the presence of the analyte in the medium.

The method may comprise coating an optical component with the functionalized organic/inorganic composite material. Measuring modulation of an optical property may comprise measuring refractive index. Measuring may comprise interrogating the optical component using fiber loop ringdown spectroscopy.

According to another aspect of the invention there is provided an optical sensor, comprising: a functionalized inorganic/organic composite material that exhibits modulation of at least one optical property upon absorption of at least one analyte; and an optical component associated with the functionalized inorganic/organic composite material that measures the modulation of the at least one optical property of the material; wherein modulation of the at least one optical property of the material is indicative of the presence of the analyte.

In some embodiments, the optical component is selected from the group consisting of tapered fiber, field access block, the respective optical components of a refractometer, the respective optical components of an ellipsometer, and long period grating. In a preferred embodiment, the optical component is a long period grating.

In some embodiments, the organic/inorganic composite material is selected from the group consisting of inorganic materials selected from metal oxides, silicates, and aluminosilicates, and combinations thereof; organic/inorganic composite polymers selected from silsesquioxanes of general structure M-R'-M, where M is a polymerizable inorganic group selected from $SiX_3$, where X=OR" or Cl or Br or I, where R" is an organic group selected from $C_nH_{2n+1}$ and an aromatic group, and R' is an organic spacer selected from an aliphatic group $(CH_2)_n$ where n is an integer from 1 to 20 optionally having substituents on the alkyl chain or an unsaturated hydrocarbon selected from alkenes, alkynes, and arenes of general formula —$C_nH_{(2n-2m)}$—, where n and m are integers from 1 to 20; and a mixture or blend of organic and inorganic materials either condensed at the same time, or physically mixed together.

The organic/inorganic composite material may be prepared by co-condensation between an inorganic silica precursor and (i) a silsesequioxane precursor selected from $X_3Si$—R'—$SiX_3$, or (ii) a siloxane terminated organic polymerizable group selected from $X_3Si$—R'—Z, where Z is a polymerizable organic group selected from acrylate and styrene, and X and R' are defined as above.

The organic/inorganic composite material may be a silsesquioxane of general structure M-R'-M, where M is as defined above and R' is —$(CH_2)_2$— or —CH=CH— or —$C_6H_4$— or $C_6H_4$—$C_6H_4$— or a combination of these, and $SiX_3$=Si$(OEt)_3$ or Si$(OMe)_3$.

The functionalized composite material may comprise a-bulk silicate material selected from the group consisting of inorganic materials selected from metal oxides, silicates, and aluminosilicates, and combinations thereof; composite polymers selected from silsesquioxanes of general structure M-R'-M or M-R'—$(Y)_n$—R'-M, where M is a polymerizable inorganic group such as a silica-based group such as $SiX_3$, where X=OR" or Cl or Br or I, where R" is an organic group such as $C_nH_{2n+1}$ or an aromatic group such as phenyl, and R' is an organic spacer which may be an aliphatic group such as —$(CH_2)_n$— where n is an integer from 1 to 20, optionally having substituents on the alkyl chain or an unsaturated hydrocarbon of any type including alkenes, alkynes, or arenes of general formula —$C_nH_{(2n-2m)}$—, where m and n are integers from 1 to 20, and Y is a group containing one or more heteroatom selected from S, N, O, P; and a mixture or blend of organic and inorganic materials either condensed at the same time, or physically mixed together.

The bulk silicate material may be prepared by co-condensation between an inorganic silica precursor and (i) a silsesequioxane precursor selected from $X_3Si$—R'—$SiX_3$, or (ii) a siloxane terminated organic polymerizable group selected from $X_3Si$—R'—Z, where Z is a polymerizable organic group selected from acrylate and styrene, where X=OR" or Cl or Br or I, where R" is an organic group such as $C_nH_{2n+1}$ or an aromatic group such as phenyl, and R' is an organic spacer which may be an aliphatic group such as —$(CH_2)_n$— where n is an integer from 1 to 20, optionally having substituents on the alkyl chain or an unsaturated hydrocarbon of any type including alkenes, alkynes, or arenes of general formula —$C_nH_{(2n-2m)}$— where m and n are integers from 1 to 20.

The bulk silicate material may be a silsesquioxane of general structure M-R'-M, where M is $SiX_3$=Si$(OEt)_3$ or Si$(OMe)_3$ and R' is —$(CH_2)_2$— or —[$CH_2$—CH($CH_3$)]— or —CH=CH— or —$C_6H_4$— or —$C_6H_4$—$C_6H_4$— or —$(CH_2)_3$—$(S)_4$—$(CH_2)_3$—, or a combination of the these.

The bulk silicate material may be formed from a monomer selected from Si$(OR)_4$ where R is an aliphatic group $(C_nH_{2n+1})$, where n is an integer from 1 to 20. In one embodiment, n=1 or 2. In one embodiment, the monomer may be TEOS (tetraethyl orthosilicate, Si$(OEt)_4$). In further embodiments, the monomer may be selected from sodium ortho silicate $Na_4SiO_4$ (or $2Na_2OSiO_2$), sodium meta silicate $Na_2SiO_3$ (or $Na_2OSiO_2$), sodium di silicate $Na_2Si_2O_5$ (or $Na_2O_2SiO_2$), and sodium tetra silicate $Na_2Si_4O_9$ (or $Na_2O_4SiO_2$).

The functionalized composite material may comprise a functional group based on an element selected from S, N, O, F, C, H, P, and combinations thereof The functionalized organic/inorganic composite material may comprise a substituted or unsubstituted functional group selected from SH, $NH_2$, PO(OH)$_2$, CO$_2$H, SR, NHR, PR$_3$, PO(OR)$_2$, NR$_2$, imidazole, benzimidazole, thiazole, POCH$_2$COR, crown ether, amide, a cyano-containing moiety, nitrile, isonitrile, sulfate, sulfonate, sulfone, sulfoxide, ester, thioester, dithioester, ether, halide, phosphate, phosphonate, phosphine, phosphite, isocyanourate, phosphonate ester, thiourea, urea, sulfide, disulfide, tetrasulfide, and combinations thereof. The functionalized composite material may comprise a functional group selected from: an aromatic group selected from phenyl, naphthyl, and anthracyl; and a saturated or unsaturated aliphatic group.

The analyte may be selected from: inorganic species selected from mercury, cadmium, lead, copper, chromium, nickel, silver, gold, rhodium, ruthenium, palladium, platinum, boron, and arsenic and their compounds; organic species selected from chlorinated hydrocarbons, simple hydrocarbons of the formula $C_nH_{2n+2}$, where n is an integer from 1 to 20, and hydrocarbon blends; cyclic hydrocarbons and unsaturated hydrocarbons of the formula $C_nH_{2n-2m}$, where n and m are integers; aromatic hydrocarbons and polycyclic aromatic hydrocarbons (PAHs); and aromatic compounds functionalized by heteroatoms including functional groups of the elements N, O, S, P, Cl and Br, either within the ring or external to the aromatic ring; and gaseous analytes in all of the above classes.

The at least one analyte may at least one metal or metal-containing compound. In a preferred embodiment, the analyte is mercury or a mercury-containing compound.

The functionalized composite material may comprise a bulk silicate material selected from bistriethoxysilane (BTESE, $(EtO)_3SiCH_2CH_2Si(OEt)_3$), TEOS ($Si(OEt)_4$), and SIS (bis[(3-triethoxysilyl)propyl]tetrasulfide, $(EtO)_3Si$—$CH_2$—$CH_2$—$CH_2$—S—S—S—S—$CH_2$—$CH_2$—$CH_2$—$Si$ $(OEt)_3$), the bulk silicate material being functionalized with at least one member selected from the group consisting of aminopropyltriethoxysilane (APTES, $(EtO)_3SiCH_2$ $CH_2CH_2NH_2$), mercaptopropyltrimethoxysilane (MPTMS, $(MeO)_3SiCH_2CH_2CH_2SH$), mercaptopropyltriethoxysilane (MPTES, $(EtO)_3SiCH_2CH_2CH_2SH$); and at least one optical property that is modulated upon absorption of at least one analyte. The functionalized composite material may be disposed as a film.

BRIEF DESCRIPTION OF THE DRAWINGS

For better understanding of the invention and to show more clearly how it may be carried into effect, reference will be made, by way of example, to the accompanying drawings which show preferred embodiments of the invention and in which.

DESCRIPTION OF PREFERRED EMBODIMENTS

Figure 1:
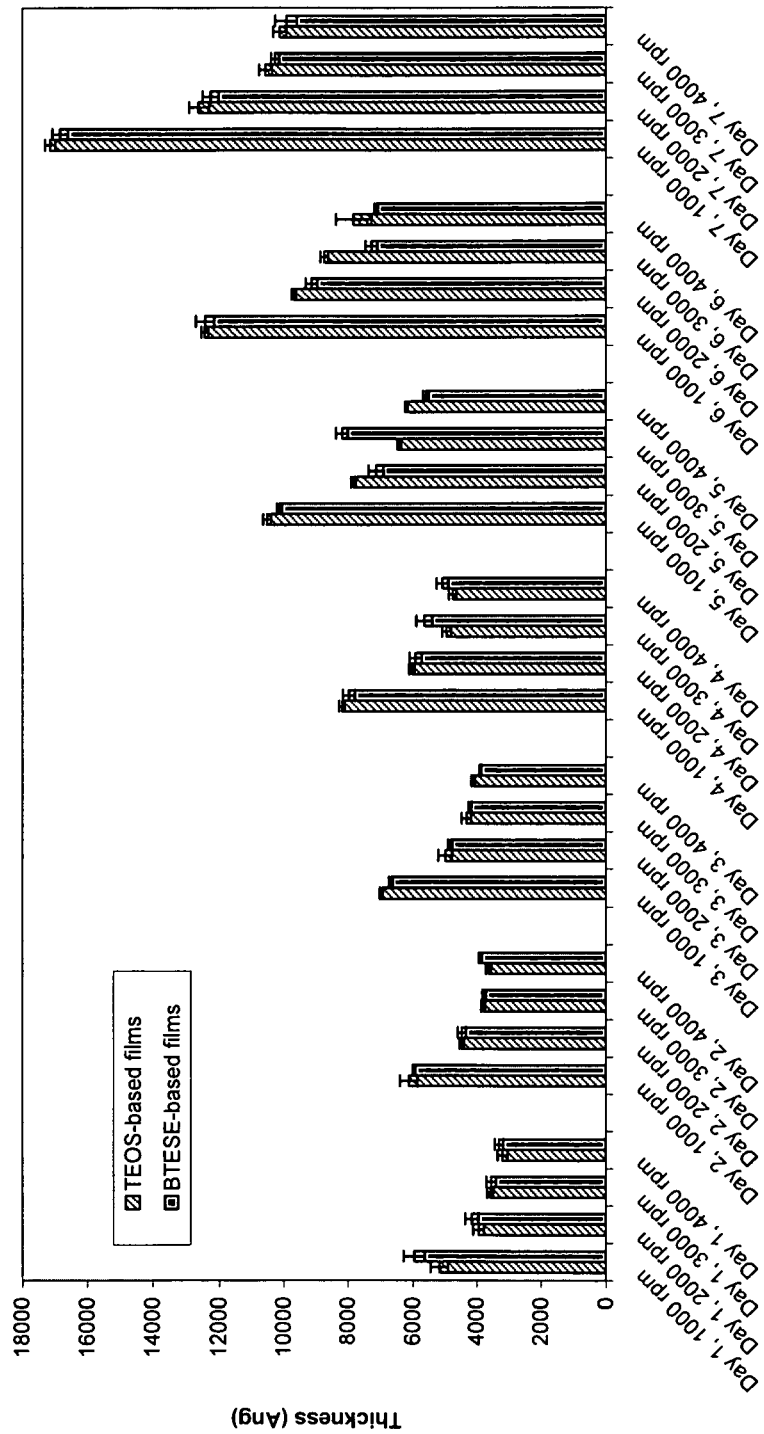
FIG. 1 shows thickness of TEOS and BTESE films functionalized with 5% MPTMS as a function of spin rate and aging time.

Functionalized organic/inorganic composite materials such as organically modified silicates (ORMOSILs) have significant potential as adsorbents, due to their ability to form complexes with a wide variety of species, and much work has focused on such use. However, use of functionalized silicates in sensing applications requires materials in specific form, for example as films (Prakash et al. 1995; Lu et al. 1996; 1997; 2003; Ogawa 1996; Brinker et al. 1999; Ogawa et al. 2000; Jung et al. 2004; Nicole et al. 2005) or monoliths (El-Safty et al. 2003a; 2003b; 2003c; 2004; 2005a; 2005b; 2005c; 2005d). Controlling physical properties of the material and at the same time preparing it in a particular morphology can be challenging.

One aspect of the invention relates to a functionalized composite material that selectively absorbs one or more analytes of interest. The functionalized composite material exhibits a change in an optical property upon absorption of the one or more analyte. The functionalized composite material is suitable for applications such as, for example, an optical sensor for detecting an one or more analytes in a medium. The invention also relates to methods of preparing such functionalized composite materials, and to preparing such materials as films. The functionalized composite materials may comprise organic and inorganic constituents, and may be referred to herein as "organic/inorganic".

As used herein, the term "absorbs" or "absorption" refers to the partitioning of an analyte into the composite material, or extraction of an analyte from the surrounding medium by the composite material. Such absorption may or may not be a reversible process. Such absorption is selective, in that non-analyte compounds present in the medium are not absorbed in any significant amount.

The functionalized composite material may comprise a bulk silicate material that is doped-with one or more functionalizing ligand. The functionalizing ligand provides absorption of one or more analyte of interest Alternatively, the functionalized composite material may comprise a bulk silicate material that itself acts as the functional group that provides absorption of the one or more analyte of interest, in which case the bulk silicate material may or may not be doped with a functionalizing ligand.

Examples of the bulk silicate material include, but are not limited to:

(1) Inorganic materials such as metal oxides, including silicates, aluminosilicates, aluminum oxide, titanium oxide, zirconium oxide, or any combination thereof. A preferred composite material is a silicate material which may be formed from monomers such as, for example, $Si(OR)_4$ where R is an organic group such as aliphatic ($C_nH_{2n+1}$), where n is an integer from 1 to 20. In one embodiment, n=1 or 2, (e.g., tetraethylorthosilicate (TEOS, $Si(OEt)_4$, where n=2). In other embodiments, R may be an aromatic group such as phenyl, naphthyl, etc. In further embodiments, the monomer may be selected from sodium ortho silicate $Na_4SiO_4$ (or $2Na_2OSiO_2$); sodium meta silicate $Na_2SiO_3$ (or $Na_2OSiO_2$); sodium di silicate $Na_2Si_2O_5$ (or $Na_2O_2SiO_2$); and sodium tetra silicate $Na_2Si_4O_9$ (or $Na_2O_4SiO_2$).

(2) Organic polymers such as polyalkyl or aryl ethylene, polyalkyleneglycol, polyacrylate, polyamide, polyether, or physical mixtures or block copolymers composed of these groups, which are functionalized with a second condensable siloxane group of the form $SiX_3$. One embodiment relates to a siloxane terminated with a polymerizable organic group such as $X_3Si$—R'-Z, where Z is the polymerizable organic group such as an acrylate or styrene group, and X and R' are defined as above. In another embodiment, the material is prepared by a co-condensation between an inorganic silica precursor and a siloxane terminated with a polymerizable organic group such as $X_3Si$—R'-Z. The inorganic silica precursor may be. TEOS. This includes organically modified silicate (ORMOSIL) type materials. In addition, the organic and inorganic polymers may be simple blends, for example a prepolymerized silicate dispersed in an organic polymer matrix.

(3a) Organic/inorganic composite polymers such as silsesquioxanes of general structure M-R'-M or M-R'—$(Y)_n$—R'-M, where M is a polymerizable inorganic group such as a silica-based group such as $SiX_3$, where X=OR" or Cl or Br or I, where R" is an organic group such as $C_nH_{2n+1}$ or an aromatic group such as phenyl, and R' is an organic spacer which may be, an aliphatic group such as —$(CH_2)_n$— where n is an integer from 1 to 20, optionally having substituents on the alkyl chain or an unsaturated hydrocarbon of any type including alkenes, alkynes, or arenes of general formula —$C_nH_{(2n-2m)}$—, where m and n are integers from 1 to 20, and Y is a group containing one or more heteroatom selected from S, N, O, P. In one embodiment, Y is S and n is 2-5. In other embodiments, the bulk component may be a silsesquioxane of general structure M-R'-M, where M is $SiX_3$=$Si(OEt)_3$ or $Si(OMe)_3$ and R' is —$(CH_2)_2$— or —[$CH_2$—$CH(CH_3)$]— or —CH=CH— or —$C_6H_4$— or —$C_6H_4$—$C_6H_4$— or —$(CH_2)_3$—$(S)_4$—$(CH_2)_3$—, or a combination of these.

(3b) Organic/inorganic composite polymers such as polyalkylsiloxanes, or polyarylsiloxanes, where the structure of the polymer is —$[SiR_2O]_n$— where R is any organic group including aromatic, aliphatic and alicyclic groups. In a preferred embodiment, R is either Me or Ph or a combination thereof.

(4) A mixture or blend of organic and inorganic materials either condensed at the same time, or physically mixed together; for example, a composite prepared by co-condensation between an inorganic silica precursor and a silsesquioxane precursor such as $X_3Si$—R'—$SiX_3$; or a co-condensation between an inorganic silica precursor and a siloxane terminated organic polymerizable group such as $X_3Si$—R'-Z, where Z is a polymerizable organic group such as an acrylate or styrene group, and X and R' are defined as above. The inorganic silica precursor may be TEOS. This includes organically modified silicate (ORMOSIL) type materials. In addition, the organic and inorganic polymers may be simple blends, for example a prepolymerized silicate dispersed in an organic polymer matrix.

According to one embodiment there is provided a functionalized composite material having at least one optical property that is modulated upon absorption of at least one analyte, comprising bistriethoxysilane (BTESE, $(EtO)_3SiCH_2CH_2Si(OEt)_3$) as a bulk material and a functional group selected from aminopropyltriethoxysilane (APTES, $(EtO)_3SiCH_2CH_2CH_2NH_2$), mercaptopropyltrimethoxysilane (MPTMS, $(MeO)_3SiCH_2CH_2CH_2SH$), mercaptopropyltriethoxysilane (MPTES, $(EtO)_3SiCH_2CH_2CH_2SH$), and combinations thereof. The functionalized composite material may be disposed as a film, which may be thin film.

According to another embodiment there is provided a functionalized composite material having at least one optical property that is modulated upon absorption of at least one analyte, comprising TEOS ($Si(OEt)_4$) as a bulk material and a functional group selected from the group consisting of aminopropyltriethoxysilane (APTES, $(EtO)_3SiCH_2CH_2CH_2NH_2$), mercaptopropyltrimethoxysilane (MPTMS, $(MeO)_3SiCH_2CH_2CH_2SH$), mercaptopropyltriethoxysilane (MPTES, $(EtO)_3SiCH_2CH_2CH_2SH$), and combinations thereof, wherein the functionalized composite material is prepared in the presence of Brij-56 surfactant. The functionalized composite material may be disposed as a film, which may be a thin film. The functionalized composite material may be disposed as a film before removal of the surfactant by extraction. The functionalized composite material may be subjected to post-extraction treatment with ammonia.

According to another embodiment there is provided a functionalized composite material having at least one optical property that is modulated upon absorption of at least one analyte, comprising bis[(3-triethoxysilyl)propyl]tetrasulfide, (SIS), $(EtO)_3Si$—$CH_2$—$CH_2$—$CH_2$—S—S—S—S—$CH_2$—$CH_2$—$CH_2$—$Si(OEt)_3$), as the bulk material. The functionalized composite material may be disposed as a film, which maybe a thin film.

The functionalized composite materials may be deposited as thick films or thin films. For the purpose of this disclosure, "thin film" is intended to mean a film that is thin on an optical scale, i.e., the film thickness is less than the wavelength of light used to interrogate the film. A film that is thicker than this is considered to be a "thick film".

Functional groups, if separate from the bulk material, may be introduced by using a reagent of the form of $X_3Si$—R'—Y or $X_3Si$—R'—Y—R'—$SiX_3$, where R' and X are defined as above and Y is a functional group based on an element selected from S, N, O, F, C, H, P, and combinations thereof. The functional group may be substituted or unsubstituted and selected from, but not limited to, SH, $NH_2$, $PO(OH)_2$, $CO_2H$, SR, NHR, $PR_3$, $PO(OR)_2$, $NR_2$, imidazole, benzimidazole, thiazole, $POCH_2COR$, crown ether, amide, a cyano-containing moiety, nitrile, isonitrile, sulfate, sulfonate, sulfone, sulfoxide, ester, thioester, dithioester, ether, halide, phosphate, phosphonate, phosphine, phosphite, isocyanourate, phosphonate ester, thiourea, urea, sulfide, disulfide, tetrasulfide, and combinations thereof The functional group, e.g., urea or thiourea, may be substituted or unsubstituted. Preferred functional groups are thiol, amine, isocyanourate, phosphonate ester, thiourea, sulfide, disulfide, tetrasulfide, and urea. In certain applications, most preferred functional groups are thiourea, urea and tetrasulfide. In addition, Y may be an aromatic group such as phenyl, naphthyl, anthracyl, or a saturated or unsaturated aliphatic group where Y=$(—CH_{2,1})_n$—H, where n is an integer between 0 and 20.

The composite materials may be prepared in the presence or absence of a structure directing agent (SDA) or surfactant, also referred to herein as a template, such as a block co-polymer or an alkylammonium group. The SDA may be a polar surfactant, e.g., consisting of a hydrophilic head and hydrophobic tail, or it may be a charged surfactant. In one embodiment, the structure directing agent may be a block co-polymer where at least one of the blocks is a polyether. In another embodiment, the SDA may be a block copolymer of the structure R—$(R'O)_n$—H, where R, R' and n are as defined above. In a preferred embodiment, the SDA may be one or more of block copolymers Pluronic F-127, Brij-76 or Brij-56. In other embodiments combinations of such SDAs or surfactants may be used.

In another embodiment, the surfactant is a tetraalkylammonium halide of structure $R_4N^+X^-$ where R is as defined above. The tetraalkylammonium halide may be $Me_3NC_{16}H_{33}^+X^-$ where X is defined as above.

The SDA may be removed by calcination at temperatures where the organic component of the composite material is stable. Preferably, the SDA is removed by extraction. For example, the SDA may be removed by extraction with an organic solvent such as ethanol. In some embodiments it is preferred that removal of the SDA is followed by treatment with ammonia Using such functionalized composite materials, it is expected that analytes including, but not limited to the following, may be sensed either individually or in combinations:

inorganic species such as mercury, cadmium, lead, copper, chromium, nickel, silver, gold, rhodium, ruthenium, palladium, platinum, boron, and arsenic and their compounds (for example, mercury may be detected in the form of elemental mercury or $HgA_2$, where A is OH, Cl, $NO_3$, Me, or a combination thereof);

organic species including chlorinated hydrocarbons such as trichloroethylene (ICE), dichloroethylene, dichloromethane, chloroform, and carbon tetrachloride; simple hydrocarbons of the formula $C_nH_{2n+2}$, where n is an integer from 1 to 20, such as methane, ethane, butane, propane, hexane, pentane, heptane, octane, or hydrocarbon blends such as gasoline or diesel fuel;

cyclic hydrocarbons and unsaturated hydrocarbons of the formula $C_nH_{2n-2m}$ such as cyclohexane, cyclohexene, hexene, and others (where n and m are integers from 1 to 20);

aromatic hydrocarbons and polycyclic aromatic hydrocarbons (PAHs) such as benzene, naphthalene, anthracene, pentacene, pyrene;

and the same class of aromatic compounds, functionalized by heteroatoms including but not limited to functional groups of the elements N, O, S, P, Cl and Br, either within the ring, such as in thiophene and pyridine, or external to the aromatic ring such as in the case of phenol, aniline, polychlorinated biphenyls (PCBs), and chlorinated dioxins and furans; and gaseous analytes in all of the above classes, including carbon dioxide, carbon monoxide, ammonia, and gaseous mercury.

In some embodiments, the at least one analyte may be at least one metal or metal-containing compound. In a preferred embodiment, the analyte is mercury or a mercury-containing compound.

Another aspect of the invention relates to the use of functionalized composite materials as described herein in optical sensor applications. The invention exploits the change in optical property of the functionalized material upon absorption of one or more analyte of interest, by measuring the change of optical property and using the measurement as an indication of the presence of the one or more analyte. The optical property may be absorbance or refractive index.

In one embodiment, the functionalized composite material is disposed as a coating, such as a thin film, on an optical component of the sensor. The optical component interrogates the functionalized composite material such that the change in optical property is detected or measured. It is expected that combinations of such materials applied to one or more optical components of a sensor may allow simultaneous detection of more than one species of analyte to be carried out, where analytical techniques such as multivariate analysis may be used to decode the information obtained from the sensor. For some applications, the functionalized composite material that is disposed onto the optical component may have narrowly-defined properties, including, for example, coating thickness, refractive index, and porosity. Thickness of the coating may be optimized for a particular application and/or analyte. It is further expected that the optimum thickness of the coating will vary depending on the refractive index of the functionalized composite material. For example, the coating may be about 1 µm to about 100 µm thick, preferably about 1 µm to about 10 µm thick, and more preferably about 1 µm to about 5 µm thick. For such applications the refractive index may be in a narrow range of about 1.44 to about 1.45. For other applications the film thickness may be specified within about 50 nm in the range of about 50 to about 1000 nm. In such applications control over the refractive index may be relaxed to greater than about 1.46.

An optical component of a sensor of the invention may be based on an optical fiber. For example, the optical component may be a fiber optic grating, such as a fiber Bragg grating (FBG). Preferably, the optical component is one which is sensitive to, or can be used to measure, refractive index. Examples of such optical components include tapered fiber, field access block, the respective optical component in a refractometer, the respective optical component in an ellipsometer, and long period grating (LPG). For example, for a refractometer, the optical component would normally be a prism, and for the ellipsometer, the optical component would be an optically flat substrate, which may be reflective. Preferably, the optical component is a long period grating.

Long period gratings, like fiber Bragg gratings, are periodic modulations of the refractive index of the core of an optical waveguide—typically a single-mode optical fiber—but the LPG has a much longer period (typically Λ=10 µm to 1 mm) compared to the Bragg grating (about Λ=1 µm or less). LPGs couple light from the mode propagating along the fiber core to co-propagating cladding modes of the fiber. Due to the high losses typically experienced by cladding modes, the LPG behaves as a notch filter. Thus, unlike FBGs, which reflect wavelengths selected by the periodicity of the grating back along the core of the optical fiber, LPGs act as notch filters with low back-reflection. Depending on the regularity of the grating period, the depth of the refractive index modulation, and the length of the grating, the band rejection of an LPG has a width of typically 30 nm and the loss at the peak can approach −30 dB (James et al. 2003, and references cited therein).

For an LPG, the wavelengths of the core modes that couple into the cladding are characterized by the phase-matching condition $$\lambda_j = \Lambda [n_{\textit{eff,core}}(\lambda, n_1, n_2) - n_{\textit{eff,cladding}}^i(\lambda, n_2, n_3)] \quad \text{(Equation 1)}$$

where $n_{\textit{eff,core}}$ is the effective core refractive index which is a function of wavelength, core refractive index $n_1$ and cladding refractive index $n_2$, and $n_{\textit{eff,cladding}}$ is the effective cladding refractive index of the $i^{th}$ mode, which is a function of wavelength, cladding refractive index $n_2$, and surrounding refractive index $n_3$, and Λ is the period of the LPG. From this expression it is apparent that any physical, mechanical, or environmental parameter that is capable of changing the effective refractive indices differentially (e.g., refractive index of the surrounding medium) or of changing the period of the grating (e.g., mechanical strain), will lead to a change in the attenuation spectrum of the LPG. Given proper calibration, one can then use the shift in the attenuation lines to interrogate the environmental parameter (James et al. 2003 and references cited therein). This measurement principle has been discussed in a number of publications, and has led to considerable interest in using LPGs as inexpensive, robust and sensitive sensors (Allsop et al. 2001; Bhatia et al. 1996; Bhatia 1999; Chong et al. 2004; DeLisa et al. 2000, Grubsky et al. 2000; James et al. 2003; Khaliq et al. 2001; 2002; Lee et al. 2003; Shu et al. 1999).

When using an LPG as a chemical sensor, the differential change in refractive index is typically induced by a change in the refractive index, $n_3$, of the medium surrounding the cladding. Since the evanescent wave of the cladding modes effectively "probes" the medium outside the fiber, its refractive index also influences the effective refractive index of the cladding. If, for example, in an extreme case where the refractive indices of cladding and surrounding bulk medium are identical, the cladding loses its ability to guide light and will essentially be extended infinitely. LPGs can hence be used as sensitive sensors for changes in refractive indices (Bhatia 1999; Chong et al. 2004; Lee et al. 2003; Shu et al. 1999). For example, aromatic compounds in a hydrocarbon matrix have been detected by changes in an LPG spectrum (Allsop et al. 2001), producing a wavelength change of ~0.4 nm for a concentration of xylene of 0.5% (vol) in a paraffin solution. The detection limit was reported as 0.04% (~400 ppm). Chemical selectivity can be achieved by flnctionalizing the surface of the fiber grating and Murphy et al. (1999) have detected bovine serum albumin in a solution of 50 mg/mL by binding to a fiber coating that was populated with reactive sites. Similarly Elster et al. (2004) demonstrated detection of Rabbit IgG from solutions between 100 μg/mL to 10 μg/mL using a Protein A coated LPG sensor. A more sensitive but less selective sensor was described by Pilla et al. (2005). A thin layer of nanoporous syndiotactic polystyrene (SPS, 250 nm thickness) was dip-coated onto an LPG. The concentration of chloroform was measured at 10 and 20 ppm. The measurement principle has been described by Starodubov (2000) for a general case of a passive coating. Here, it was assumed that the medium outside the fiber extends indefinitely—an approximation that holds as long as the film thickness is much larger than the penetration depth of the evanescent wave.

Thus, an LPG has spectral characteristics that are very sensitive to the refractive index of the surrounding medium. In accordance with the invention, this sensitivity is exploited by coating the LPG with a functionalized composite material that is capable of absorbing one or more analytes of interest. As the coating material extracts the analyte from the surrounding medium (e.g., a liquid or gas phase), the refractive index of the coating changes and the attenuation spectrum of the LPG shifts in a predictable way. For films with a thickness greater than about 1 to 5 μm the highest sensitivity is obtained when the refractive index n of the coating is matched to that of the fiber, e.g., for n=1.44 to 1.46 in the case of a fused silica fiber, such as that used in the example below. For films that are thinner than about 1 μm, the LPG spectrum may still show a pronounced shift in the attenuation spectrum if the refractive index is higher than that of the cladding (Rees, 2002; Del Villar, 2005).

Any suitable technique may be employed for measuring the refractive index of the coated LPG so as to sense the presence of an analyte in a medium. In some embodiments, ring-down spectroscopy may be employed, such as the fiber loop ring-down spectroscopy (FLRDS) techniques described in U.S. Pat. No. 6,842,548, issued Jan. 11, 2005 and in copending U.S. patent application Ser. No. 11/079,478, filed Mar. 15, 2005, and U.S. patent application Ser. No. 11/145, 182, filed Jun. 6, 2005.

For an LPG-based sensor with a functionalized composite material as a film coating, the film preferably has the following characteristics: a refractive index and thickness matched to the specifications of the grating and the fiber optic cable; free of large cracks; hydrolytically stable; and functionalized with one or more groups capable of absorbing an analyte (or analyte class) of interest, the functionalizing group(s) being accessible throughout the entire material. In an embodiment suitable for detecting one or more metals such as copper, mercury, lead, cadmium, platinum, and palladium, the film may comprise a material composed of, for example, bistriethoxysilane (BTESE, $(EtO)_3SiCH_2CH_2Si(OEt)_3$), tetraethoxysilane (TEOS, $Si(OEt)_4$), bis[(3-triethoxysilyl)propyl] tetrasulfide (SIS), and/or $(EtO)_3Si$—$CH_2CH_2CH_2$—$S$—$S$—$S$—$S$—$CH_2CH_2CH_2Si(OEt)_3$), which may be further modified with a functional group, such as aminopropyltriethoxysilane (APTES, $(EtO)_3SiCH_2CH_2CH_2NH_2$) and its derivatives, mercaptopropyltrimethoxysilane (MPTMS, $(MeO)_3SiCH_2CH_2CH_2SH$), or mercaptopropyltriethoxysilane (MPTES, $(EtO)_3SiCH_2CH_2CH_2SH$).

Other materials showing a change in the attenuation spectra when applied to an LPG as a thin film have been described by Rees et al. (2002) and Ishaq et al. (2005) (Langmuir-Blodgett Film of tricosenic acid, not used for sensing), by Cusano et al. (2005) and Giordano et al. (2004) (syndiotactic polystyrene film, measured response to chloroform in water), and Wang et al. (2005) (ionic self-assembled monolayers, not used for sensing).

In initial investigations three classes of materials were selected as candidates for coatings for an optical sensor, and heavy metals, particularly mercury, were targeted as examples of analytes for detection. The materials were: (1) mesoporous silicates prepared by co-condensation of TEOS and MPTMS or MPTES in the presence of either Pluoronic F-127, $[EO_{97}PO_{67}EO_{97}]$, where EO is ethylene oxide and PO is propylene oxide, or Brij-57, $[H_{33}C_{16}\text{-}(EO)_{10}H]$ where EO is defined as above; (2) silsesquioxane materials based on BTESE [2] along with the MPTMS or MPTES in the presence and absence of an SDA; and (3) bis[(3-triethoxysilyl)propyl] tetrasulfide (SIS), $(EtO)_3Si$—$CH_2CH_2CH_2$—$S$—$S$—$S$—$S$—$CH_2CH_2CH_2$—$Si(OEt)_3$) which acts as both the bulk material and sensing agent, in the presence and absence of an SDA, and in the presence and absence of added TEOS.

Brinker et al. (1999) reported the preparation of thin films composed of BTESE and TEOS in the presence of Brij-56 surfactant with the addition of BTESE (up to 75:25 molar ratio). In this case, increasing the amount of BTESE led to improved mechanical properties (Fan et al. 2000; 2001). Addition of BTESE is also known to improve hydrothermal stability (Liu et al. 2005). Oviatt et al. (1993) demonstrated that BTESE based silicates have high surface areas, and can be mesoporous depending on the synthesis conditions. In addition, Shea et al. (2003a; 2003b) showed that phenylene-bridged thiol-doped materials are mesoporous and have a large capacity for mercury. Xiang et al. (2003) showed that a composite material composed of bis[(3-triethoxysilyl)propyl]tetrasulfide (SIS), $(EtO)_3Si$—$CH_2CH_2CH_2$—$S$—$S$—$S$—$S$—$CH_2CH_2CH_2Si(OEt)_3$) at only 15% loading with TEOS, prepared with SDA $EO_{20}PO_{70}EO_{20}$, had a remarkable capacity for mercury absorption, with each sulfur atom binding to 2-3 mercury atoms. The material, even at 15% loading, had an uptake capacity of 2.7 g of mercury per gram of material.

Synthesis, characterization, absorption of mercury and the resulting change in optical properties of the materials, and a functional optical sensor for detecting mercury using an LPG are shown in the following non-limiting examples. The results indicate the utility of functionalized composite materials such as silicate films in optical sensor applications. The results also suggest the importance of effective removal of surfactant in films prepared with a surfactant. It is expected that two types of film coatings will be particularly useful for optical sensors of the invention. Those are (1) coatings having a thickness in excess of 2 μm and having a refractive index that is matched to the cladding material of the LPG (for fused silica waveguides typically n=1.44 to 1.46), and (2) coatings having a refractive index larger than that of the fiber material, but with a thickness that is chosen to provide for a large shift of the attenuation maxima upon absorption of analyte into the film. For the second case, theoretical models have-been developed that predict at which film thicknesses the position of the peaks in attenuation spectrum is most sensitive to refractive index changes of the high refractive index coating. (Del Villar et al. 2005, and references cited therein).

The experimental results suggest that procedures aimed at introducing and/or increasing porosity, and/or improving removal of the surfactant, will decrease the refractive index. TEOS-based films have been reported to have refractive indices in the range of 1.15 to 1.30 in air (Wirnsberger et al. 2000; Yang et al. 2000). Filling of the pores with water will increase the refractive indices of the films, and the addition of, e.g., polarizable aromatic or tetrasulfide groups, will further increase the refractive indices to the desired range for thick films. The refractive index is therefore a function of the porosity, surfactant loading, and chemical composition of the film material.

EXAMPLE 1

Preparation of Silicate Materials of Low Refractive Index Using BTESE (No Template) or TEOS with Pluorinc F-127

Sol Preparation

Functionalized silicates were prepared employing BTESE (2) or TEOS as the monomer and MPTES or MPTMS as the functional group of type $X_3Si-R'-Y$, where X=OEt or OMe, $R'=-CH_2CH_2CH_2-$ and Y=SH. Loading of the material with thiol is given as the mol % of the thiol relative to the total. The TEOS-based materials were all prepared with Pluronic F-127 as the surfactant/structure-directing agent, since under appropriate conditions it gives cubic films which provide access to pores perpendicular to the surface of the film, unlike hexagonal silicates which predominantly form films with pores oriented parallel to the surface (Grosso et al. 2001).

High-quality unfunctionalized films have been prepared with F-127 surfactants (Zhao et al. 1998a; Zhao et al. 1998c). As noted above, BTESE-based materials were prepared using F-127, but additional films were prepared without surfactant since these materials have been reported to be porous even without the presence of surfactant (Oviatt et al. 1993).

For a typical sol containing 5% thiol, ethanol (20 mL) was added to a glass jar containing a stirbar and Pluronic F-127 (1 g). The jar was capped and stirred at room temperature for 20 min to completely dissolve the surfactant and produce a clear solution. To this solution was added premixed silica precursors of desired ratios, TEOS (2.12 mL) or BTESE (1.78 mL) and MPTMS (0.09 mL). HCl, aq, 1M (1 mL) was added and the capped jar was stirred for 30 min. The cap was then removed and the sol was allowed to age up to 7 days prior to casting.

When a two-step preparation was employed (Nitta, Pisupatti et al., 1999), the initial hydrolysis of the siloxane precursor was performed under acidic conditions and then the reaction made basic (approximately pH 9) using $NH_4OH$ before spin coating.

Two-Step Preparation of BTESE Film

For a sol containing 10% thiol, BTESE (1.814 mL, 4.897 mmol), MPTES (0.131 mL, 0.5441 mmol,) and HCl, aq (0.294 mL, 20 mM) were added to ethanol (1.22 mL) and stirred at 60° C. for approximately 90 min. The sol was cooled to room temperature and subsequently made basic through the addition of $NH_4OH$, aq, (0.33 mL, 50 mM) and the sol was immediately used for coating substrates.

Film Preparation

The films were prepared by spin coating sols composed of monomer, thiol, structure-directing agent (if added) in aqueous ethanol solutions. After mixing surfactant and silicate precursors, the resulting mixture was aged at room temperature for up to 7 days before spin coating. In some cases, a two-step preparation was employed (Nitta et al. 1999), where the initial hydrolysis of the siloxane precursor was performed under acidic conditions, and then the reaction made basic (approximately pH 9) using $NH_4OH$ before spin coating. All sols were pre-filtered through a 45 μm filter prior to spin coating to ensure that any particulates in the sol were removed. Approximately 0.05 mL of sol was deposited onto a clean, silicon wafer which was spun at 1000-3000 rpm to ensure a smooth film.

After spin coating, the films were aged at 90° C. in air. In those cases where surfactant was used, its extraction was attempted by treatment with ethanolic HCl (500 mL ethanol, 1.17 g concentrated HCl) for 17 h at room temperature prior to aging of the films.

Film Thickness

The effect of spinning rate and aging time on film thickness was assayed and is shown in Table 1 and FIG. 1 for films prepared with TEOS and BTESE using F-127 as the surfactant, with 5% MPTMS as the thiol component. Film thickness was determined before extraction of the surfactant by profilometry using a surface profilometer. Ellipsometry was also employed and select films were examined after extraction of the surfactant.

TABLE 1

Film thickness as a function of aging time and spin rate

| Film | Aging time (d) | Spin rate (rpm) | Film thickness (nm) TEOS | BTESE |
|---|---|---|---|---|
| 1 | 1 | 1000 | 518 | 596 |
| 2 | 1 | 2000 | 394 | 415 |
| 3 | 1 | 3000 | 358 | 356 |
| 4 | 1 | 4000 | 320 | 331 |
| 5 | 2 | 1000 | 613 | 597 |
| 6 | 2 | 2000 | 447 | 447 |
| 7 | 2 | 3000 | 380 | 377 |
| 8 | 2 | 4000 | 363 | 389 |
| 9 | 3 | 1000 | 697 | 669 |
| 10 | 3 | 2000 | 499 | 484 |
| 11 | 4 | 1000 | 819 | 797 |
| 12 | 4 | 2000 | 604 | 593 |
| 13 | 5 | 1000 | 1053 | 1014 |
| 14 | 5 | 2000 | 783 | 714 |
| 15 | 6 | 1000 | 1242 | 1241 |
| 16 | 6 | 2000 | 969 | 913 |
| 17 | 7 | 1000 | 1715 | 1684 |
| 18 | 7 | 2000 | 1259 | 1226 |

Refractive Index Determination

Figure 2:
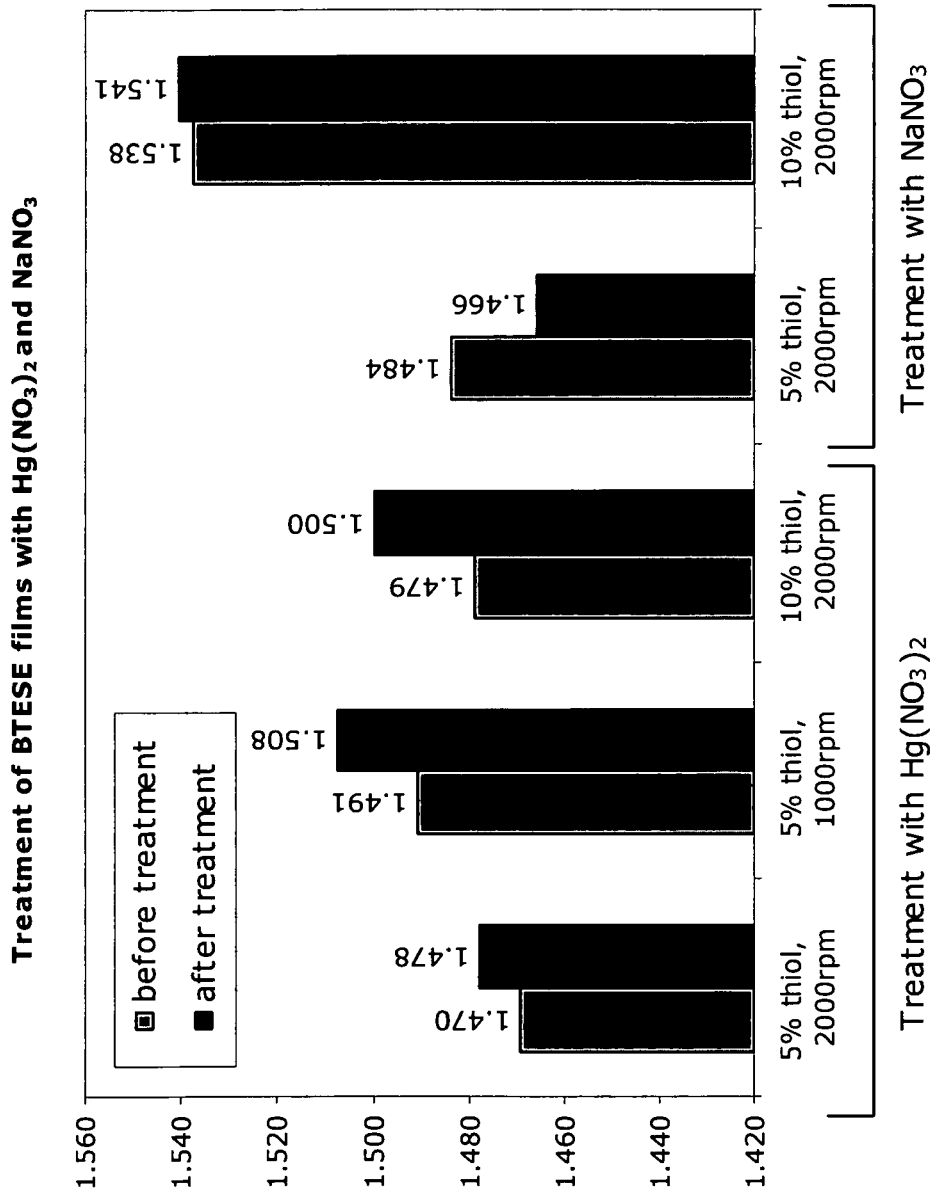
FIG. 2 shows measured refractive index of BTESE films prepared without surfactant, before and after treatment with $Hg(NO_3)_2$ or $NaNO_3$.

BTESE-based films were also prepared without Pluronic F-127 template and their thickness and refractive indices measured by scanning ellipsometry. In this case, the two-step procedure described above was employed for the preparation of the sol. Base ($NH_4OH$) was added to approximately pH 9 to speed up the condensation reactions, which are more facile at high pH, and thus reduce the need to age the sols prior to coating. The amount of thiol added was adjusted from 5 to 20%. Results are shown in FIG. 2 and Table 2. As expected, increasing spin rates led to thinner films. In addition, for a given spin rate, increasing the thiol loading caused an increase in the refractive index of the film. This increase is linear only if the Lorenz-Lorentz equation holds and the additional thiol groups do not affect the structure of the material.

TABLE 2

Film thickness and refractive index in BTESE films prepared without Pluronic F-127

| Film | Spin rate (rpm) | Thiol loading | Film thickness (nm) | Refractive index |
|---|---|---|---|---|
| 1 | 2000 | 5% | 1659 | 1.470 |
| 2 | 1000 | 5% | 2433 | 1.491 |
| 3 | 2000 | 10% | 1543 | 1.479 |
| 4 | 1000$^a$ | 20% | 2205 | 1.496 |

$^a$Estimated spin rate.

Mercury Uptake

The ability of films to absorb mercury was determined by exposing films to a solution of $Hg(NO_3)_2$ in water. The concentration of mercury in water before and after treatment was assayed by cold vapour atomic absorption. Exposure of a TEOS-5% MPTMS film to a 0.1 ppm solution resulted in a decrease in concentration of mercury to 18 ppb. This corresponds to an uptake of 4.1 µg of mercury from a 50 mL solution containing 5 µg, for a total scavenging of 82% of the total mercury. Since the film dimensions were about 15 mm×25 mm×500 nm, the total volume of the material was estimated at 180 nL. Therefore, 22 g of mercury was absorbed for every liter of the film. The partition coefficient was calculated as pKfs=6.1.

Millimeter-thick films prepared by allowing the sol to gel in a Petri dish showed much higher levels of mercury uptake. For example, a 50 mL $Hg(NO_3)_2$ solution with a concentration of 11 ppm (550 µg Hg) was reduced to 0.028 ppm, corresponding to removal of 548.7 µg Hg. This is a removal of 99.75% of the mercury, and is significant since it demonstrates that mercury is also somewhat absorbed into the interior of the material, and not just on the surface of a thin film. The partition coefficient was only pKfs=5.1, indicating that 10 times fewer thiol sites were accessible in the thick film compared to the thin film.

Effect of Mercury Uptake on Optical Properties

The effect of mercury exposure on the refractive index of the BTESE films prepared without Pluronic F-127 is shown in FIG. 2. The starting refractive indices of the films varied from 1.47 to 1.49. However, all films responded to mercury treatment with an increase in refractive index, while exposure to sodium nitrate gave only a slight decrease in the refractive index. For example, a film prepared with 5% thiol, spun at 1000 rpm, had an initial refractive index of n=1.491 which increased to n=1.508 upon treatment with $Hg(NO_3)_2$ (FIG. 2).

Figure 3:
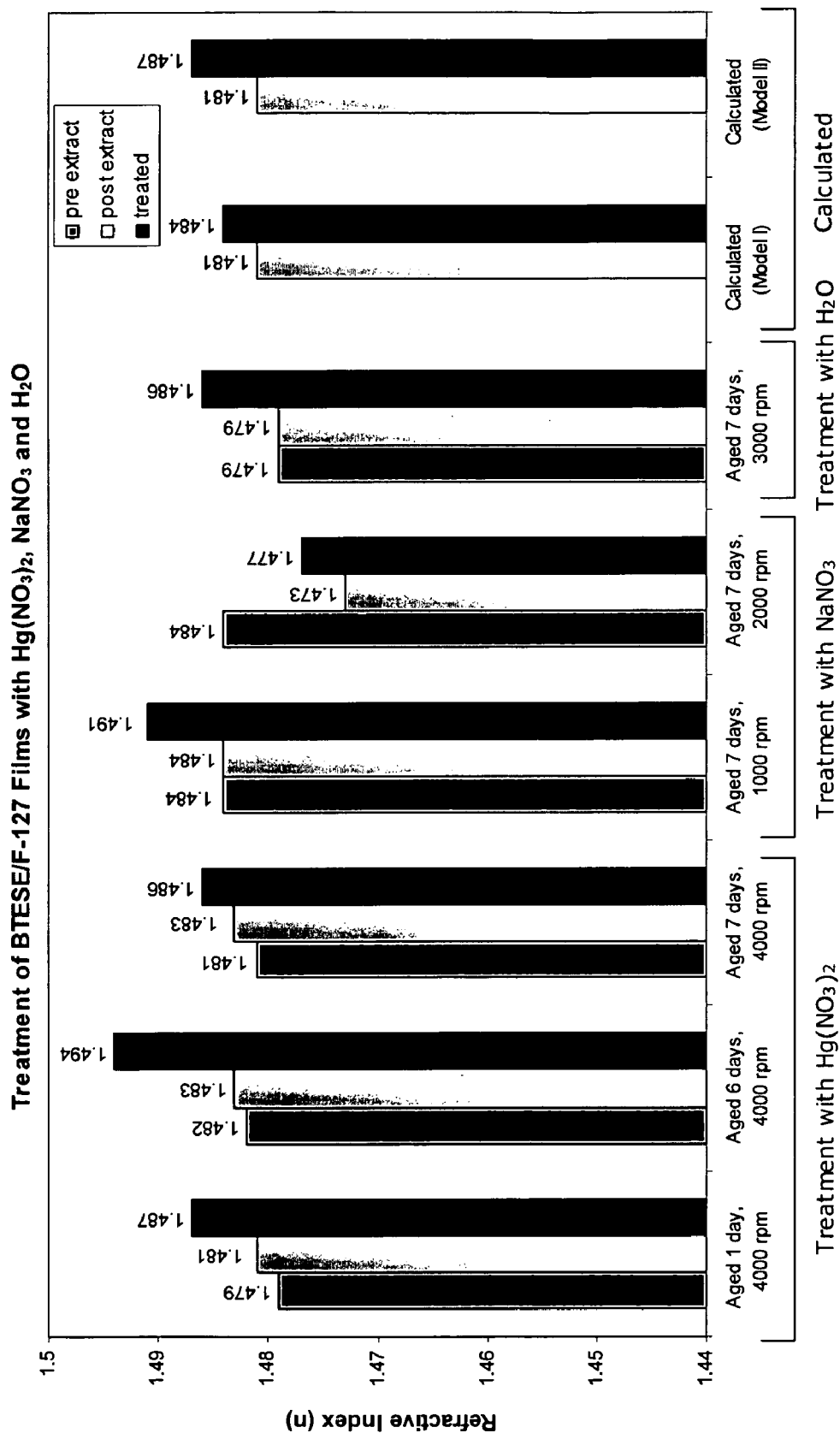
FIG. 3 shows measured and calculated refractive index of BTESE films prepared using surfactant (Pluronic F-127), before (pre-extract) and after (post-extract) removal of the surfactant, and after treatment (treated) with $Hg(NO_3)_2$, $NaNO_3$, or $H_2O$; calculated refractive index based on the Lorentz-Lorenz equation where the polarizability of $Hg^{2+}$ was assumed to be 1.25 $A^3$ (Model I) or 6.3 $A^3$ (Model II)

Refractive index data for films that were prepared from BTESE and F-127 as the template are shown in FIG. 3. Refractive index was measured before and after template removal, and after treatment with mercury nitrate. As a control, the refractive indices of films were also measured after treatment with aqueous solutions of $NaNO_3$ and Millipore water.

As shown in FIG. 3, refractive indices of the films were relatively consistent at about 1.48, regardless of thickness or aging time. Exposure of films to $Hg(NO_3)_2$ resulted in all cases in an increase in refractive index to approximately 1.49. Although a similar increase was noted upon exposure to aqueous sodium nitrate, the response in this case was within experimental error for the ellipsometry measurement ($\delta n=\pm 0.005$ on both measurements). Considering this error, the only change in refractive index in FIG. 3 that was statistically significant was the second entry (aged 6 days, 4000 rpm), where a 0.011 increase in refractive index was observed upon treatment with mercury. Solid state $^{13}C$ NMR and elemental analysis indicated that Pluronic F-127 remained in the film at a level of about 38 wt-%. Thus, it is expected that a more complete removal of the surfactant will increase availability of pores for uptake of mercury, leading to even larger increases in the refractive index of the film. In addition, higher thiol loadings have been demonstrated to improve capacity and speed of uptake (Bibby et al. 2002).

Calculation of the Expected Refractive Index Change

For one of the films (5% thiol) the expected refractive index was estimated from atomic polarizability data using the Lorenz-Lorentz equation $$\frac{n^2-1}{n^2+2} = \frac{4\pi}{3} \sum \frac{M_i}{V} \alpha_i \qquad \text{(Equation 2)}$$

where the fractional density $M_i/V$ was calculated from the composition of the film and the mass-weighted ionic polarizability (in L/kg). The ionic polarizability volume of $\alpha'(O)=1.7\ A^3$ was obtained from Tessman et al. (1953) and $\alpha'(Si)=3.2\ A^3$ was determined from Equation 2 using a density of $SiO_2$ of $\rho=1.6$ kg/L (Williford et al. 2005) and a refractive index of n=1.45. Assuming an identical value for the density of the BTESE (5% thiol) film, its refractive index was calculated as n(BTESE)=1.481 using the ionic polarizability $\alpha'(S)=4.8\ A^3$ and assuming negligible contributions from carbon and hydrogen. After exposure to $Hg(NO_3)_2$ solution, the film was loaded to about 1% by weight with mercury—considerably below the limiting value of 13.6% predicted if each sulfur atom was bound to one mercury atom. Using an ionic polarizability of $\alpha'(Hg^{2+})=1.25\ A^3$, a refractive index change of $\Delta n=3.5\ 10^{-3}$ to n(BTESE-Hg)=1.484 was calculated. The limiting value of n=1.486 for 13.6% loading corresponds to a change that is only slightly larger. The model assumes that ionic polarizabilities are additive, which is not necessarily the case for covalent bonding of mercury. Also, it was assumed that the volume of the film remained constant and that the polarizability of the matrix did not change upon uptake of mercury. However, we note that the estimate for the refractive index appears low. When using the polarizability of neutral mercury, $\alpha'(Hg^0)=6.3\ A^3$, which is a value that is comparable to $\alpha'(Pb^{2+})=4.9\ A^3$ in PbO, refractive indices of n=1.487 (n=1.519) are obtained for a loading of 1% (13.6%). Although rough, this estimate confirms that an LPG sensor capable of detecting refractive index changes of $\Delta n=10^{-4}$ is capable of detecting low-ppb concentrations of $He^{2+}$.

Use of Functionalized Silicate-Coated LPGs as Hg(II) Sensors

Having demonstrated that thiol-containing BTESE films absorb mercury, and do so with a change in their refractive indices, we then coated an LPG with a BTESE/thiol film. This film was made without using surfactant. To coat the LPG, a polytetrafluoroethylene PTFE holder (used to align the LPG while coating and hold the coating sol) was designed and built in-house. The part of the fiber that contained the LPG was first exposed to a 1 M KOH$_{(aq)}$ solution for 0.5 h to etch the surface of the fiber and expose surface silanol groups. The etched fiber was then aligned and secured across the 4 mL-capacity well of the PFTE holder, and once the sol had aged for approximately 85% of its total gelation time, the sol was transferred to the well. The LPG was immersed in the sol for about 15 minutes to allow reaction between the sol and the surface silanol groups of the fiber. The LPG was then pulled from the well and the coating was dried under ambient conditions for 24 h before curing in an oven at 90° C. for an additional 24 h. After curing, the coated fiber was used as synthesized (i.e., the templating surfactant was left in the film matrix). The PTFE holder mentioned above was used to hold aqueous solutions of different mercury concentrations during the sensing tests.

The attenuation spectra (FIG. 4) were recorded in straight transmission mode using a broad band light source in combination with a commercial spectrum analyzer. When exposing the LPGs to solutions they were mounted in a trough which was capable of holding a few mL of solution.

Figure 4:
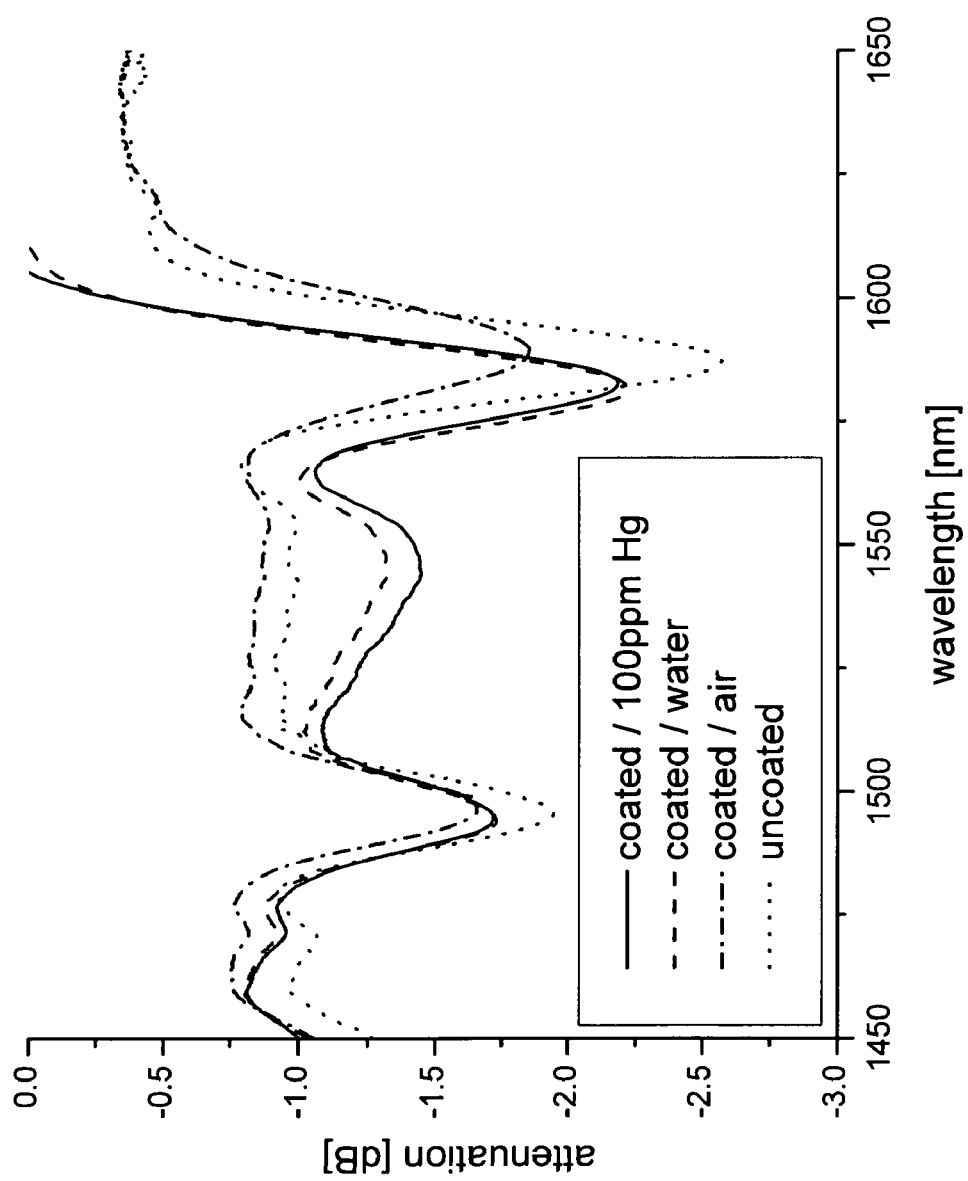
FIG. 4 shows the attenuation spectrum of a long period grating ($\Lambda$=274 µm) without a film coating and exposed to air, and coated with a BTESE film (prepared without surfactant) and exposed to air, water, or 100 ppm aqueous $Hg(NO_3)_2$ solution.

The key peak in the spectrum in air shifted from a wavelength of λ=1588 nm (uncoated) to 1589 nm (coated). Exposure of the coated LPG to water resulted in a significant 8 nm shift to 1581 nm. It should be noted that exposure of an uncoated LPG to water results in a shift of less than 1 nm. Subsequent exposure to a 100 ppm solution of mercury nitrate resulted in an additional shift to 1582 nm. The spectra and resultant shifts are shown in FIG. 4.

Figure 5:
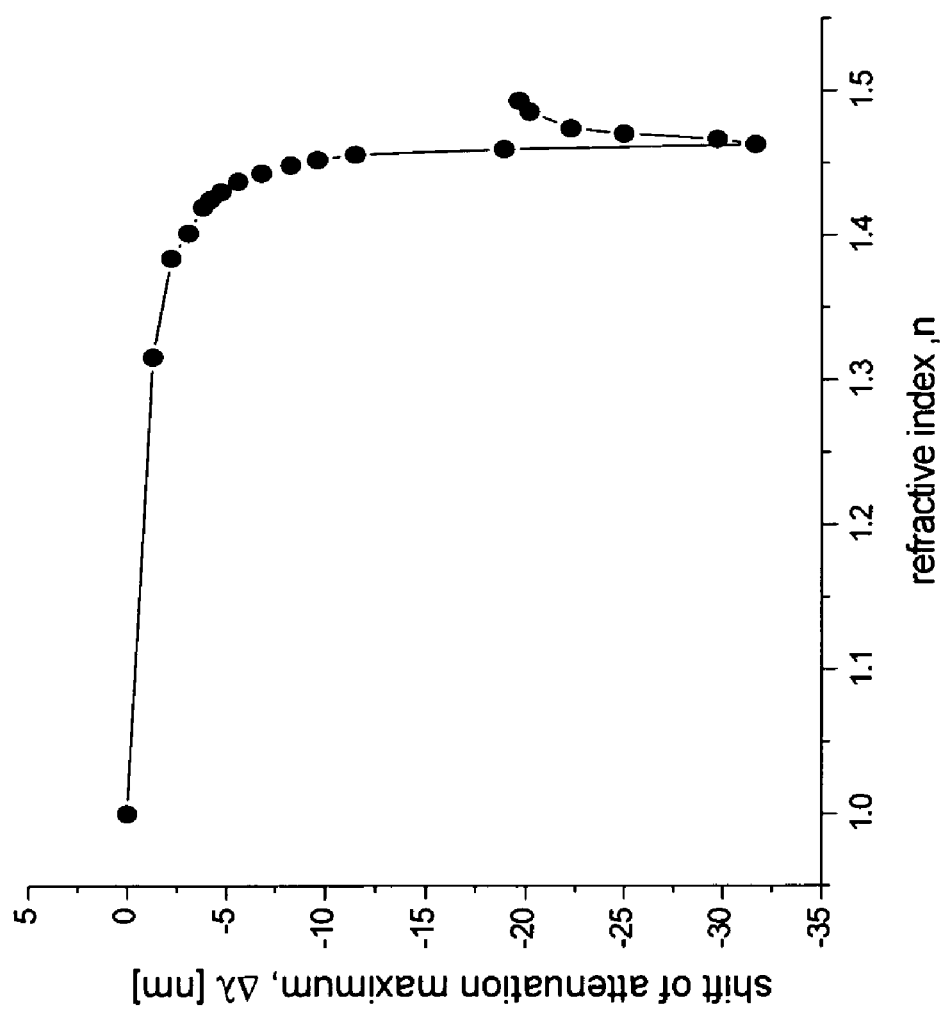
FIG. 5 is a plot of the shift of the attenuation maximum at $\lambda\approx1590$ nm of an uncoated long period grating ($\Lambda$=274 µm) having a cladding refractive index of about 1.46, as a function of the refractive index of the environment, with respect to the attenuation maximum of the same uncoated grating in air.

The shift to longer wavelength upon increase of refractive index can be understood considering the calibration curve for films that have a thickness in excess of about 2 μm (FIG. 5). Examination of FIG. 5 revealed that when an LPG is coated with such a thick film having a refractive index of about n=1.48 (in water), the attenuation maximum of the LPG will shift to a higher wavelength as the refractive index of the coating is increased (here, by absorption of mercury). The Figure also shows that only coatings that have a refractive index of n<1.44 in water will display a shift to lower wavelengths upon uptake of mercury. When applying such thick films this lower refractive index is preferred since the slope to the low-RI side of the wavelength shift maximum (at n=1.45) is better defined and corresponds to sharper peaks in the attenuation spectra. In this regime the cladding modes have not yet lost their ability to guide light, whereas at refractive indices larger than the RI of the cladding, the cladding modes become lossy and attenuation spectra are broader.

Figure 6:
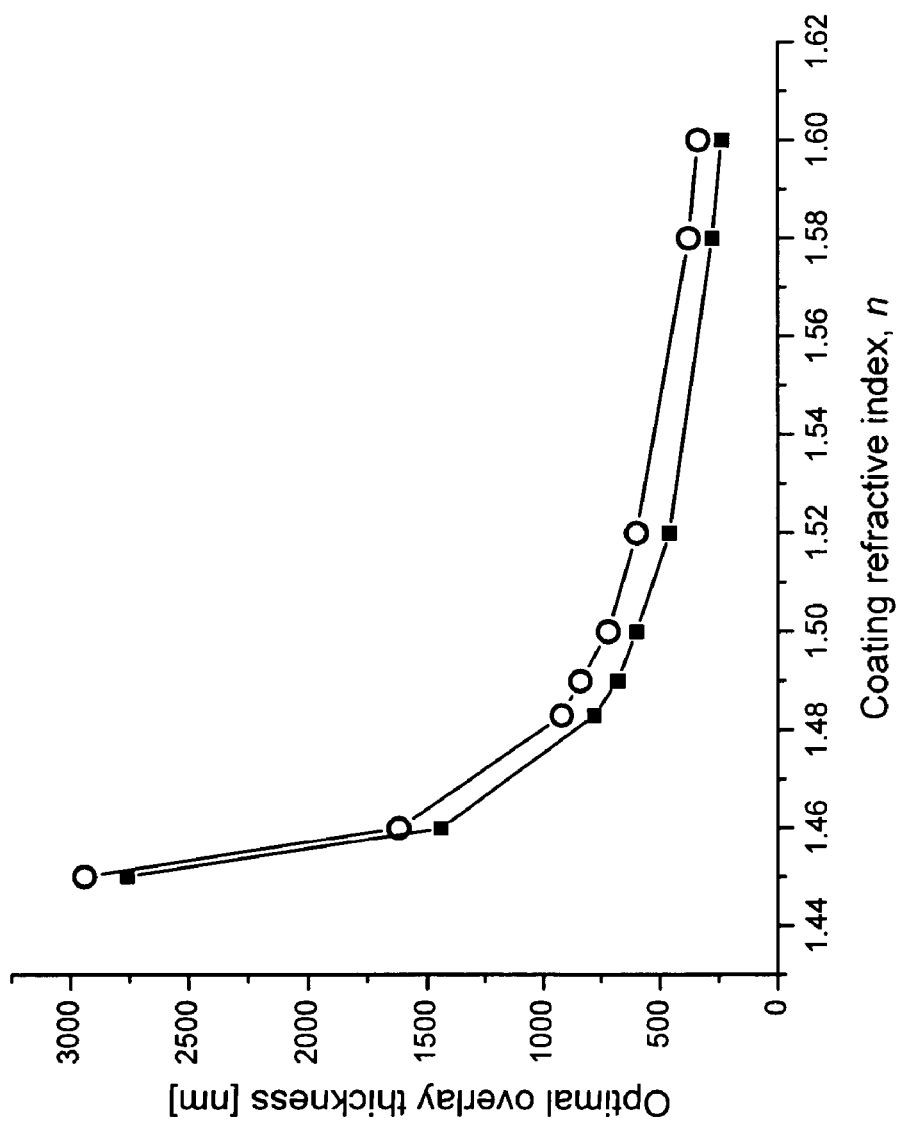
FIG. 6 shows the relationship between film thickness and refractive index. The thickness most sensitive to changes in the refractive index is the thickness at which the first cladding mode (LP02 mode) is lost into the environment, if the environment is air (circles) or water (squares)

Alternatively, a film with high refractive index, such as the one described, here, will perform as a chemical sensor if the thickness is controlled in such a way that the shift in the attenuation maxima with refractive index change is maximized. Preliminary work provides an estimate of the film thickness—for a given refractive index—at which the largest spectral shift is obtained upon change of that refractive index. This estimate is given in FIG. 6, which shows the film thickness at which the lowest cladding mode (LP02) undergoes a transition from being guided to being unguided by the cladding, in air and in water. Note that this correlation between optimal thickness and refractive index is only the lowest of multiple curves.

EXAMPLE 2

Rapid Preparation of Films Using Ionic Surfactants (CTAB)

Sol Preparation

A more rapid sol preparation has also been employed based on Hatton et al. (2005) where the ionic structure directing agent cetyltrimethylammonium bromide (CTAB, 0.2604 g) was dissolved in an acidic aqueous ethanolic solution (0.69 g water; 0.71 g HCl, aq, $10^{-3}$ M; EtOH 1.15g), which was combined with the pre-mixed silica monomers BTESE and MPTMS (0.84 g and 0.02 g respectively). After stirring and aging for 4 h, the resulting sol was coated onto desired substrates (glass or silicon) and air-dried overnight. The material with surfactant had a refractive index of 1.479. The surfactant was then removed by solvent extraction using methanol and hydrochloric acid for 2 h.

Film Preparation

Spin-Coating: Substrates (glass or silicon) were cleaned by soaking in 1 M NaOH$_{(aq)}$ for 20 minutes, 1 M HCl$_{(aq)}$ for 5 minutes, and then rinsed thoroughly in Millipore® water before drying with a stream of nitrogen gas. To coat the substrates, 0.05 mL of sol were deposited on the substrate and the substrates were typically spin-coated at 3000 rpm for 10 s to create thick, but even, films. The films were then air dried at room temperature overnight. Any remaining sol was left to gel completely into monoliths.

Dip-Coating: LPG-inscribed fibers were threaded through an in-house fabricated PTFE container designed to hold the coating sol yet allow middle sections of fiber to be coated (as opposed to the fiber termini). An LPG was lowered into the sol at 5 mm/s, followed by 10 s of immersion in the sol, and was finally withdrawn from the sol at a rate of 5-10 mm/s (rate of withdrawal depended on the desired film thickness). The films were then air-dried at room temperature overnight. Any remaining sol was left to gel completely into monoliths for further characterization.

Post-Synthetic Treatment

After air-drying the bulk material (recovered from a Petri dish) at room temperature overnight, it was transferred to a sealed chamber with an atmosphere of saturated ammonia vapor and aged for 36 h.

The surfactant was then removed by solvent extraction using methanol (200 mL) and concentrated hydrochloric acid (12 mL) for 2 h at 55° C.

The resulting bulk material was mesoporous with BET surface area of 906 m$^2$/g with a narrow pore size distribution of about 26.1 Å.

Refractive Index Determination

The refractive index of the film coated on a silicon wafer and prior to NH$_3$ treatment and solvent extraction was 1.479 as determined from an average of scanning ellipsometric measurements.

EXAMPLE 3

Preparation of Low Refractive Index Silicates (5 mol % MPTMS/95 mol % TEOS and Templated with Brij® 56)

Sol Preparation.

Brij® 56 (0.5993 g, 8.774×10$^{-4}$ mol) was dissolved in anhydrous ethanol (1184 g, 0.257 mol) before adding TEOS (2.2392 g, 0.0107 mol), MPTMS (0.1105 g, 5.63×10$^{-4}$ mol), aqueous HCl (0.5 mL of 6 M solution) and Millipore® water (0.5 mL). The contents were stirred for an additional 10 minutes before letting the sol age statically at room temperature overnight in the fume hood. The following day, the sol was viscous enough to use for spin-coat or dip-coat films.

Film Preparation

Spin-Coating: Substrates (glass or silicon) (20×20 mm) were cleaned by soaking in 1 M NaOH$_{(aq)}$ for 20 minutes, 1 M HCl$_{(aq)}$ for 5 minutes, and then rinsed thoroughly in Millipore® water before drying with a stream of nitrogen gas. To coat the substrates, 0.05 mL of sol were deposited on the substrate and the substrates were typically spin-coated at 3000 rpm for 10 s to create thick, but even, films. The films were then left to air-dry at room temperature overnight. Any remaining sol was left to gel completely into monoliths.

As can be seen in Table 3, the refractive indices of the extracted films dropped considerably compared for materials that still contained the template (in this case Brij®-56). However, the film thickness was retained within 80% of the original (surfactant included) films. Films that were not treated with ammonia tended to have pore adsorption to the surface.

TABLE 3

Refractive Indices and Thicknesses of Films Before and After Extraction of the Surfactant.

| Organic Loading | As-Synthesized Film Thickness [nm] | As-Synthesized Refractive Index at 1551 nm | Extracted Film Thickness [nm] | Extracted Refractive Index at 1551 nm |
|---|---|---|---|---|
| 5 mol % MPTMS | 564 | 1.4679 | 465 | 1.3041 |
| 20 mol % APTES | 494 | 1.4839 | 393 | 1.3628 |
| 20 mol % APTES[a] | 2473 | 1.4664 | 2506 | <1.42 |

[a]Values for refractive index were obtained from the refractometer, so the extracted refractive index could not be determined because the value was outside the range of the refractometer (i.e. 1.42-1.50).

Dip-Coating: LPG-inscribed fibers were threaded through an in-house fabricated PTFE container designed to hold the coating sol yet allow middle sections of fiber to be coated (as opposed to the fiber termini). An LPG was lowered into the sol at 5 mm/s, followed by 10 s of immersion in the sol, and was finally withdrawn from the sol at a rate of 5-10 mm/s (rate of withdrawal depended on the desired film thickness). The films were then left to air-dry at room temperature overnight Any remaining sol was left to gel completely into monoliths for further characterization.

Post-Synthetic Treatment

After air-drying at room temperature overnight, films were transferred to a sealed chamber with an atmosphere of saturated ammonia vapor (resulting from the vaporization of concentrated ammonium hydroxide at room temperature). Films were left to age in the chamber for approximately 2 h before transferring the films to an oven to dry overnight at 90° C. Bulk material was left to age in ammonia atmosphere for at least 6 h before transferring to the oven to dry at 90° C. overnight.

For solvent extraction the films were placed in a round-bottom flask in 80 mL of anhydrous ethanol and 10 mL of 9 M HCl$_{(aq)}$ under reflux for 1 day. Bulk material was subjected to solvent extraction under the same conditions for 2 days.

Figure 7:
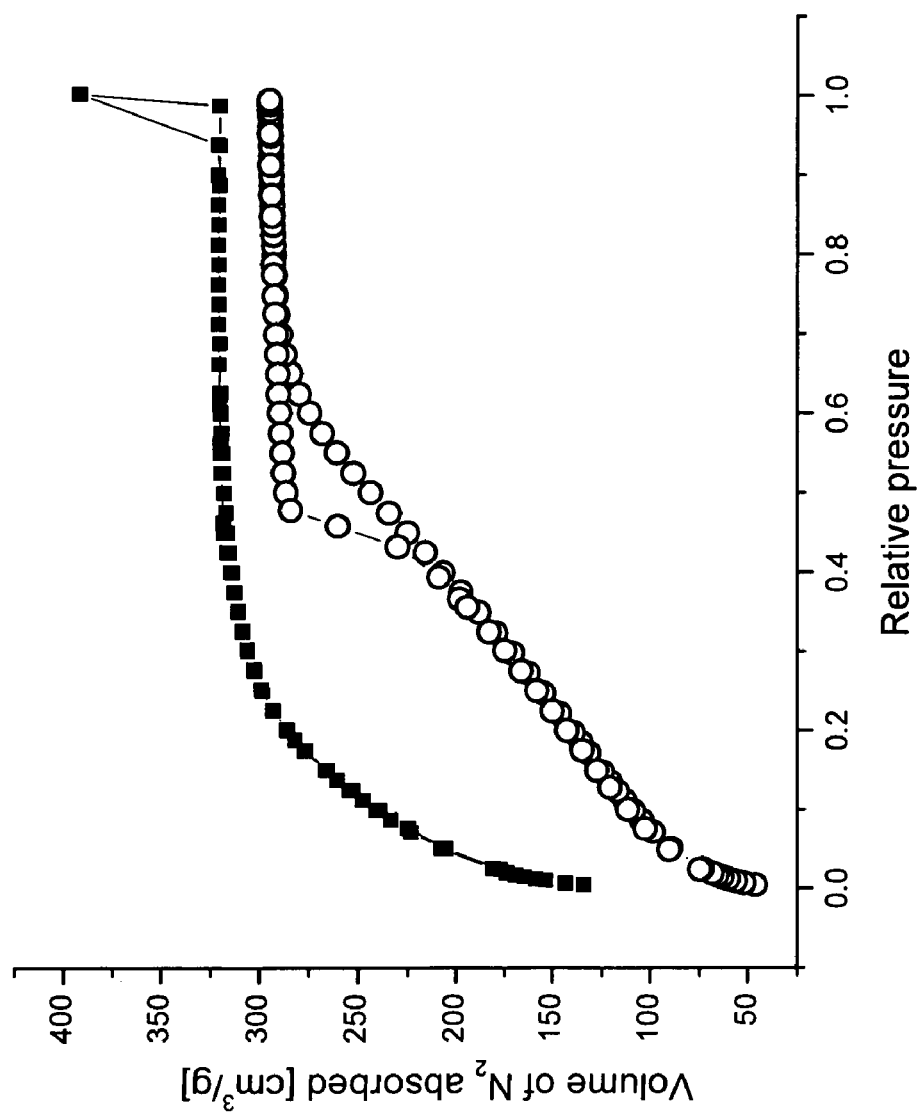
FIG. 7 shows absorbed nitrogen as a function of partial pressure for mesoporous JD102 functionalized material (5% MPTMS, 95% TEOS, templated with Brij-56) before (filled squares) and after (empty circles) treatment with ammonia.

The films were removed from the solvent and dried in the oven at 90° C. for approximately 2 h. The bulk extracted material was collected by vacuum filtration and dried in the oven at 90° C. overnight Refractive Index Determination The refractive indices of films prepared on silicon wafers were measured by ellipsometry, and the thicknesses of the films were determined by profilometry and confirmed by ellipsometry for entries 1 and 2. The effect of the ammonia treatment is to increase condensation in the walls and to improve the pore structure, changing the material from microporous to mesoporous (FIG. 7). The surface area of the material before treatment was 1050 m$^2$/g and the pore size was 17 Å, indicating that the material was microporous. The surface area after treatment was 544 m$^2$/g since mesoporous materials have smaller surface areas than microporous materials, and the pore size was 34 Å.

Mercury Uptake

The 5% MPTMS material was examined for its ability to take up mercury. After treatment of a 40 mL solution of initial concentration of 0.84 ppm Hg with a single thin film material, the Hg content was decreased to 0.33 ppm, demonstrating the ability of the material to take up mercury from an aqueous solution.

EXAMPLE 4

Procedure for Preparation of High Refractive Index Silicates (100 mol % SIS, No Surfactant)

Bis[(3-triethoxysilyl)propyl]tetrasulfide (SIS) (0.219 g, 4.06×10$^{-4}$ mol), anhydrous ethanol (3.16 g, 0.0686 mol), and HCl$_{(aq)}$ (0.06 mL of a 0.11 M solution) were added to a flask and sonicated at room temperature for 15 minutes The sol was then aged statically at room temperature overnight before being used to either spin-coat or dip-coat substrates (20×20 mm). To prepare thicker films, the substrates were coated repeatedly, allowing 1 day between consecutive coatings to ensure that the previous layer was sufficiently dry prior to depositing additional layers. Each layer was dried at room temperature.

As shown in Table 4, the increase in film thickness was uniformly 90±3 nm after deposition of the first layer. As layers were added the increasing thickness was observed by the refraction of light caused by the different thickness films, where films changed colour from layer to layer.

TABLE 4

Repeated spin-coating of high refractive index thin films for thickness control

| Number of Coats | Film Thickness [nm] | Refractive Index at 1551 nm |
|---|---|---|
| 1 | 130 | 1.5732 |
| 2 | 219 | 1.5758 |
| 3 | 292 | 1.5745 |
| 4 | 389 | 1.5751 |

As shown in Table 5, the refractive indices of films prepared even with small amounts of SIS were significantly higher than those prepared with MPTMS, even at higher loadings of the latter. Films prepared without surfactant at 100% loading of SIS have refractive indices of 1.57, which are in the range of films that can be employed as high refractive index thin films, according to the method of Del Villar et al. (2005).

TABLE 5

Change in refractive index of silicate films as a function of change in organic content in the silicate

| Organic Loading in As-Synthesized Films | Refractive Index at 1551 nm |
|---|---|
| 5 mol % MPTMS/95 mol % TEOS/Brij 56 | 1.4664 |
| 10 mol % MPTMS/90 mol % TEOS/Brij 56 | 1.4952 |
| 5 mol % SIS/95 mol % TEOS/Brij 56 | 1.5198 |
| 100 mol % SIS (no surfactant) | 1.5746 |

Mercury Uptake

The 100 mol % SIS material was examined for its ability to take up mercury. After treatment of 40 mL of a solution of initial concentration of 0.84 ppm Hg with a single thin film (20×20 mm), the Hg content was decreased to 0.57 ppm. Therefore, even though it was non porous, the film showed the ability to absorb mercury.

The contents of all cited patents, patent applications, and publications are incorporated herein by reference in their entirety.

While the invention has been described with respect to illustrative embodiments thereof, it will be understood that various changes may be made in the embodiments without departing from the scope of the invention. Accordingly, the described embodiments are to be considered merely exemplary and the invention is not to be limited thereby.

REFERENCE LIST

Aguado, J., J. Arsuaga, et al. (2005). "Adsorption of Aqueous Mercury(II) on Propylthiol Functionalized Mesoporous Silica Obtained by Co-Condensation." Industrial & Engineering Chemistry Research 44: 3665-3671.

Al-Abadleh, H. A., A. B. Voges, et al. (2004). "Chromium (VI) Binding to Functionalized Silica/Water Interfaces Studied by Nonlinear Optical Spectroscopy." Journal of the American Chemical Society 126: 11126-11127.

Allsop, T., Zhang, L., and Bennion, I.(2001), "Detection of Organic Aromatic Compounds in Paraffin by a Long-Period Fiber Grating Optical Sensor With Optimized Sensitivity", Optics Communications, 191, 3-6, p. 181 ff.

Antochshuk, V. and M. Jaroniec (2002). "1-allyl-3-propylthiourea modified mesoporous silica for mercury removal." Chemical Communications(3): 258-259.

Antochshuk, V., O. Olkhovyk, et al. (2003). "Benzoylthiourea-modified mesoporous silica for mercury(II) removal." Langmuir 19(7): 3031-3034.

Baney, R. H., M. Itoh, et al. (1995). "Silsesquioxanes." Chemical Reviews 95(5): 1409-1430.

Beck, J. S., J. C. Vartuli, et al. (1992). "A New Family of Mesoporous Molecular-Sieves Prepared with Liquid-Crystal Templates." Journal of the American Chemical Society 114(27): 10834-10843.

Bertolo, J. M., A. Bearzotti, et al. (2005). "X-rays and electrical characterizations of ordered mesostructurated silica thin films used as sensing membranes." Sensors and Actuators B-Chemical 111: 145-149.

Bhatia, V. and Vengsarkar, A. M.(1996), "Optical Fiber Long-Period Grating Sensors", Optics Letters, 21, 9, p. 692.

Bhatia, V.(1999), "Applications of Long-Period Gratings to Single and Multi-Parameter Sensing", Optics Express, 4, 11, p. 457.

Bibby, A. and L. Mercier (2002). "Mercury(II) ion adsorption behavior in thiol-functionalized mesoporous silica microspheres." Chemistry of Materials 14(4): 1591-1597.

Brinker, C. J., Y. F. Lu, et al. (1999). "Evaporation-induced self-assembly: Nanostructures made easy." Advanced Materials 11(7): 579.

Chong, J. H., Shum, P., Haryono, H., Yohana, A., Rao, M. K, Lu, C., and Zhu, Y. N.(2004), "Measurements of Refractive Index Sensitivity Using Long-Period Grating Refractometer", Optics Communications, 229, 1-6, p. 65.

Crudden, C. M., M. Sateesh, et al. (2005). "Mercaptopropyl-modified mesoporous silica: A remarkable support for the preparation of a reusable, heterogeneous palladium catalyst for coupling reactions." Journal of the American Chemical Society 127: 10045.

Cusano, A. P. Pilla, A. Iadiciccio, S. Campopiano, A. Cutolo, M. Giordano, G. Guerra, (2005) "High-sensitivity optical chemosensor based on coated long-period gratings for sub-ppm chemical detection in water", Applied Physics Letters, 87, 234105.

DeLisa, M. P., Zhang, Z., Shiloach, M., Pilevar, S., Davis, C. C., Sirkis, J. S., and Bentley, W. E.(7-1-2000), "Evanescent Wave Long Period Fiber Bragg Grating As an Immobilized Antibody Biosensor", Analytical Chemistry, 72, 13, p. 2895 ff.

Del Villar, I., I. R. Matias, F. J. Arregui, P. Lalanne (2005), "Optimization of sensitivity in long-period fiber gratings with overlay deposition", Optics Express, 13, 1, 56.

Del Villar, I., I. R. Matias, F. J. Arregui (2006), "Influence on cladding mode distribution of overlay deposition on long-period fiber gratings", Journal of the Optical Society of America A, 23, 3 651.

El-Safty, S. A. and T. Hanaoka (2003a). "Fabrication of crystalline, highly ordered three-dimensional silica monoliths (HOM-n) with large, morphological mesopore structures." Advanced Materials 15(22): 1893.

El-Safty, S. A. and T. Hanaoka (2003b). "Monolithic nanostructured silicate family templated by lyotropic liquid-crystalline nonionic surfactant mesophases." Chemistry of Materials 15(15): 2892-2902.

El-Safty, S. A. and T. Hanaoka (2003c). "Synthesis of monolithic nanostructured silicate family materials through the lyotropic liquid crystalline mesophases of non-ionic surfactant." Nanotechnology in Mesostructured Materials 146: 173-176.

El-Safty, S. A. and T. Hanaoka (2004). "Microemulsion liquid crystal templates for highly ordered three-dimensional mesoporous silica monoliths with controllable mesopore structures." Chemistry of Materials 16(3): 384-400.

El-Safty, S. A., T. Hanaoka, et al. (2005a). "Design of highly stable, ordered cage mesostructured monoliths with controllable pore geometries and sizes." Chemistry of Materials 17(12): 3137-3145.

El-Safty, S. A., T. Hanaoka, et al. (2005b). "Large-scale design of cubic Ia3d mesoporous silica monoliths with high order, controlled pores, and hydrothermal stability (vol 17, pg 47, 2005)." Advanced Materials 17(4): 392-392.

El-Safty, S. A., F. Mizukami, et al. (2005c). "General and simple approach for control cage and cylindrical mesopores, and thermal/hydrothermal stable frameworks." Journal of Physical Chemistry B 109(19): 9255-9264.

El-Safty, S. A., F. Mizukami, et al. (2005d). "Transparent cubic Fd3m mesoporous silica monoliths with highly controllable pore architectures." Journal of Materials Chemistry 15(26): 2590-2598.

Elster, J., Jones, M. E., Pennington, C. D., Averett, J. P., and Bryant, J. L. (2004), "Fiber-Optic Flow Cell and Method Relating Thereto" U.S. patent application, issued May 6, 2004. 2004/0086216 A1.

Etienne, M. and A. Walcarius (2003). "Analytical investigation of the chemical reactivity and stability of aminopropyl-grafted silica in aqueous medium." Talanta 59(6): 1173-1188.

Fan, H. Y., Y. F. Lu, et al. (2000). "Rapid prototyping of patterned functional nanostructures." Nature 405(6782): 56-60.

Fan, H. Y., S. Reed, et al. (2001). "Hierarchically structured functional porous silica and composite produced by evaporation-induced self-assembly." Microporous and Mesoporous Materials 44: 625-637.

Feng, X., G. E. Fryxell, et al. (1997). "Functionalized monolayers on ordered mesoporous supports." Science 276(5314): 923-926.

Fryxell, G. E., J. Liu, et al. (1999). "Design and Synthesis of Selective Mesoporous Anion Traps." Chemistry of Materials 11: 2148-2154.

Gier, T. E., X. H. Bu, et al. (1998). "Synthesis and organization of zeolite-like materials with three-dimensional helical pores." Nature 395(6698): 154-157.

Giordano, M, M. Russo, A. Cusano, A. Cutolo, G. Mensitieri, and L. Nicolais (2004) "Optical Sensor based on ultrathin films of δ-form syndiotactic polystyrene for fastand high resolution detection of chloroform", Applied Physics Letters, 85, 22, 5349.

Grosso, D., A. R. Balkenende, et al. (2001). "Two-dimensional hexagonal mesoporous silica thin films prepared from black copolymers: Detailed characterization amd formation mechanism." Chemistry of Materials 13(5): 1848-1856.

Grubsky, V. and Feinberg, J.(2000), "Long-Period Fiber Gratings With Variable Coupling for Real-Time Sensing Applications", Optics Letters, 25, 4, p. 203 ff.

Hanzel, R. and P. Rajec (2000). "Sorption of cobalt on modified silica gel materials." Journal of Radioanalytical and Nuclear Chemistry 246(3): 607-615.

Hatton, B. D., Landskron, K. et al. (2005) "Spin Coated Periodic Mesoporous Organosilica Thin Films-Towards a New Generation of Low-Dielectric-Constant Materials." 15 (2) Advanced Funcational Materials, 15 (2), 823-829.

Hossain, K. Z. and L. Mercier (2002). "Intraframework metal ion adsorption in ligand-functionalized mesoporous silica." Advanced Materials 14(15): 1053.

James, S. W. and Tatam, R. P.(2003), "Optical Fibre Long-Period Grating Sensors: Characteristics and Application", Measurement Science & Technology, 14, 5, p. R49.

Jung, J. I., J. Y. Bae, et al. (2004). "Preparation and characterization of structurally stable hexagonal and cubic mesoporous silica thin films." Journal of Sol-Gel Science and Technology 31(1-3): 179-183.

Kang, T., Y. Park, et al. (2003). "Functionalized mesoporous adsorbents for Pt(II) and Pd(II) adsorption from dilute aqueous solution." Nanotechnology in Mesostructured Materials 146: 527-530.

Kang, T., Y. Park, et al. (2004a). "Ordered mesoporous silica (SBA-15) derivatized with imidazole-containing functionalities as a selective adsorbent of precious metal ions." Journal of Materials Chemistry 14(6): 1043-1049.

Kang, T., Y. Park, et al. (2004b). "Highly selective adsorption of $Pt^{2+}$ and $Pd^{2+}$ using thiol-functionalized mesoporous silica." Industrial & Engineering Chemistry Research 43(6): 1478-1484.

Khaliq, S., James, S. W., and Tatam, R. P.(2001), "Fiber-Optic Liquid-Level Sensor Using a Long-Period Grating", Optics Letters, 26, 16, p. 1224.

Khaliq, S., James, S. W., and Tatam, R. P.(2002), "Enhanced Sensitivity Fibre Optic Long Period Grating Temperature Sensor", Measurement Science & Technology, 13, 5, p. 792.

Lee, S. T., Kumar, R. D., Kumar, P. S., Radhakrishnan, P., Vallabhan, C. P. G., and Nampoori, V. P. N.(2003), "Long Period Gratings in Multimode Optical Fibers: Application in Chemical Sensing", Optics Communications, 224, (4-6): 237.

Lee, U. H., M. H. Kim et al. (2006) "Mesoporous thin films with accessible pores from surfaces", Bulletin of the Korean Chemical Society, 27, (6): 808-816.

Lim, M. H. and A. Stein (1999). "Comparative studies of grafting and direct syntheses of inorganic-organic hybrid mesoporous materials." Chemistry of Materials 11(11): 3285-3295.

Liu, J., X. D. Feng, et al. (1998a). "Hybrid mesoporous materials with functionalized monolayers." Chemical Engineering & Technology 21(1): 97-100.

Liu, J., X. D. Feng, et al. (1998b). "Hybrid mesoporous materials with functionalized monolayers." Advanced Materials 10(2): 161.

Liu, A. M., K. Hidajat, et al. (2000). "A new class of hybrid mesoporous materials with functionalized organic monolayers for selective adsorption of heavy metal ions." Chemical Communications(13): 1145-1146.

Liu, J., Q. Yang, et al. (2005). "Structural Relation Properties of Hydrothermally Stable Functionalized Mesoporous Organosilicas and Catalysis." Journal of Physical Chemistry B 109: 12250-12256.

Loy, D. A. and K. J. Shea (1995). "Bridged Polysilsesquioxanes—Highly Porous Hybrid Organic-Inorganic Materials." Chemical Reviews 95(5): 1431-1442.

Loy, D. A., J. P. Carpenter, et al. (1999). "Cyclization phenomena in the sol-gel polymerization of alpha,omega-bis (triethoxysilyl)alkanes and incorporation of the cyclic structures into network silsesquioxane polymers." Journal of the American Chemical Society 121(23): 5413-5425.

Lu, Y. F., L. Han, et al. (1996). "Chemical sensors based on hydrophobic porous sol-gel films and ATR-FTIR spectroscopy." Sensors and Actuators B-Chemical 36(1-3): 517-521.

Lu, Y. F., R. Ganguli, et al. (1997). "Continuous formation of supported cubic and hexagonal mesoporous films by sol gel dip-coating." Nature 389(6649): 364-368.

Lu, Y. F., B. F. McCaughey, et al. (2003). "Aerosol-assisted formation of mesostructured thin films." Advanced Materials 15(20): p. 1733.

Makkuni, A., L. G. Bachas, et al. (2005). "Aqueous and vapor phase mercury sorption by inorganic oxide materials functionalized with thiols and poly-thiols." Clean Techniques and Environmental Policy 7: 87-96.

McCool, B. A. and W. J. DeSisto (2005). "Amino-Functionalized Silica Membranes for Enhanced Carbon Dioxide Permeation." Advanced Functional Materials 15: 1635-1640.

Mercier, L. and T. J. Pinnavaia (1997). "Access in mesoporous materials: advantages of a uniform pore structure in the design of a heavy metal ion adsorbent for environmental remediation." Advanced Materials 9: 500.

Mercier, L. and T. J. Pinnavaia (1998). "Heavy metal Ian adsorbents formed by the grafting of a thiol functionality to mesoporous silica molecular sieves: Factors affecting Hg(II) uptake." Environmental Science & Technology 32(18): 2749-2754.

Metivier, R., I. Leray, et al. (2005). "A mesoporous silica functionalized by a covalently bound calixarene-based fluoroionophore for selective optical sensing of mercury(II) in water." Journal of Materials Chemistry 15: 2965-2973.

Moscatelli, A., A. Galarneau, et al. (2004). "Hosting Ability of Mesoporous Micelle-Templated Silicas toward Organic Molecules of Different Polarity." Journal of Physical Chemistry B 108: 18580-18589.

Murphy, K. E. and Jones, M. E.(1999), "Optical Fiber Long Period Sensor Having a Reactive Coating" U.S. Pat. No. 5,864,641, issued Jan. 26, 1999.

Naik, S. P., S. Yamakita, et al. (2004). "Studies on mesoporous silica films synthesized using F127, a triblock copolymer." Microporous and Mesoporous Materials 75(1-2): 51-59.

Nam, K. H. and L. L. Tavlarides (2005). "Synthesis of a High-Density Phosphonic Acid Functional Mesoporous Adsorbent: Application to Chromium(III) Removal." Chemistry of Materials 17: 1597-1604.

Nicole, L., C. Boissiere, et al. (2005). "Mesostructured hybrid organic-inorganic thin films." Journal of Materials Chemistry 15(35-36): 3598-3627.

Nitta, S. V., Pisupatti, V., Jain, A., Wayner, P. C., Gill, W. N., and Plawsky, J. L. (1999), "Surface Modified Spin-on Xerogel Films As Interlayer Dielectrics", Journal of Vacuum Science & Technology B, 17, 1, p. 205 ff.

Ogawa, M. (1996). "A simple set-gel route for the preparation of silica-surfactant mesostructured materials." Chemical Communications(10): 1149-1150.

Ogawa, M. and N. Masukawa (2000). "Preparation of transparent thin films of lamellar, hexagonal and cubic silica-surfactant mesostructured materials by rapid solvent evaporation methods." Microporous and Mesoporous Materials 38(1): 35-41.

Olkhovyk, O., V. Antochshuk, et al. (2004). "Benzoylthiourea-modified MCM-48 mesoporous silica for mercury(II) adsorption from aqueous solutions." Colloids and Surfaces a-Physicochemical and Engineering Aspects 236(1-3): 69-72.

Olkhovyk, O., V. Antochshuk, et al. (2005a). "Thermogravimetric studies of benzoylthiourea-modified MCM41 after adsorption of mercury ions from aqueous solutions." Analyst 130(1): 104-108.

Olkhovyk, O. and M. Jaroniec (2005b). "Periodic Mesoporous Organosilica with Large Heterocyclic Bridging Groups." Journal of the American Chemical Society 127: 60-61.

Olkhovyk, O., S. Pikus, et al. (2005c). "Bifunctional periodic mesoporous organosilica with large heterocyclic bridging groups and mercaptopropyl ligands." Journal of Materials Chemistry 15: 1517-1519.

Oviatt, H. W., K. J. Shea, et al. (1993). "Alkylene-Bridged Silsesquioxane Sol-Gel Synthesis and Xerogel Characterization—Molecular Requirements for Porosity." Chemistry of Materials 5(7): 943-950.

Pilla, P., Iadicieco, A., Contessa, L., Campopiano, S., Cutolo, A., Giordano, M., Guerra, G., and Cusano, A. (2005), "Optical Chemo-Sensor Based on Long Period Gratings Coated With Delta Form Syndiotactic Polystyrene", IEEE Photonics Technology Letters, 17, 8, p. 1713 ff.

Prakash, S. S., C. J. Brinker, et al. (1995). "Silica Aerogel Films Prepared at Ambient-Pressure by Using Surface Derivatization to Induce Reversible Drying Shrinkage (Vol 374, Pg 439, 1995)." Nature 375(6530): 431-431.

Rees, N. D., S. W. James, R. P. Tatam, G. J. Ashwell, "Optical fiber long-period gratings with Langmuir-Blodgett thin-film overlays" Optics Letters, 686-688, 2002.

Sayen, S., C. Gerardin, et al. (2003). "Electrochemical detection of copper(II) at an electrode modified by a carnosine-silica hybrid material." Electroanalysis 15(5-6): 422-430.

Schaefer, D. W., G. Beaucage, et al. (2004). "Structure of arylene-bridged polysilsesquioxane xerogels and aerogels." Chemistry of Materials 16(8): 1402-1410.

Schroden, R. C., M. Al-Daous, et al. (2002). "Hybrid macroporous materials for heavy metal ion adsorption." Journal of Materials Chemistry 12(11): 3261-3267.

Shea, K. J., Hobson, S. T., and Tran, J. (2003a), "Hybrid Organic-Inorganic Adsorbents", International Patent Application No. PCT/US02/09856 (WO 03/055452).

Shea, K. J., Hobson, S. T., and Tran, J. (2003b), "Hybrid Organic-Inorganic Adsorbents, U.S. Patent Application Publication No. US2003/0176396 A1.

Shu, X. W. and Huang, D. X. (1999), "Highly Sensitive Chemical Sensor Based on the Measurement of the Separation of Dual Resonant Peaks in a 100-μm Period Fiber Grating", Optics Communications, 171, 1-3, p. 65.

Starodubov, D.(2000), "Optical Fiber Sensors, Tunable Filters and Modulators using Long-Period Gratings", U.S. Pat. No. 6,058,226, issued May 2, 2000.

Tessman, J. R., Kahn, A. H., and Shockley, W. (1953), "Electronic Polarizabilities Of Ions In Crystals", Physical Review, 92, 4, p. 890.

Trens, P., M. L. Russell, et al. (2002). "Preparation of malonamide-MCM-41 materials for the heterogeneous extraction of radionuclides." Industrial & Engineering Chemistry Research 41(21): 5220-5225.

Venkatesan, K. A., T. G. Srinivasan, et al. (2003). "Removal of complexed mercury by dithiocarbamate grafted on mesoporous silica." Journal of Radioanalytical and Nuclear Chemistry 256(2): 213-218.

Walcarius, A., J. Devoy, et al. (1999). "Electrochemical Recognition of Selective Mercury Adsorption on Minerals." Environmental Science & Technology 33: 4278-4284.

Wang, Z., J. R. Heflin, R. H. Stolen, S. Ramachandran (2005). "Analysis of optical response of long-period fiber gratings to nm-thick thin-film coatings", Optics Express 13, 8 2808.

Wen, J. Y. and G. L. Wilkes (1996). "Organic/inorganic hybrid network materials by the sol-gel approach." Chemistry of Materials 8(8): 1667-1681.

Williford, R. E., X. S. Li, et al. (2005). "Mechanical stability of templated mesoporous silica thin films." Microporous and Mesoporous Materials 85(3): 260-266.

Wirnsberger, G. and G. D. Stucky (2000). "Microring Lasing from Dye-Doped Silica/Block Copolymer Nanocomposites." Chemistry of Materials 12: 2525-2527.

Yang, P., G. Wirnsberger, et al. (2000). "Mirrorless. Lasing from Mesostructured Waveguides Patterned by Soft Lithography." Science 287: 465-467.

Yantasee, W., Y. H. Lin, et al. (2003). "Nanoengineered electrochemical sensor based on mesoporous silica thin-film functionalized with thiol-terminated monolayer." Analyst 128(7): 899-904.

Yantasee, W., Y. Lin, et al. (2004). "Simultaneous detection of cadmium, copper, and lead using a carbon paste electrode modified with carbamoylphosphonic acid self-assembled monolayer on mesoporous silica (SAMMS)." Analytica Chimica Acta 502: 207-212.

Yantasee, W., L. A. Deibler, et al. (2005a). "Screen-printed electrodes modified with functionalized mesoporous silica for voltammetric analysis of toxic metal ions." Electrochemistry Communications 7: 1170-1176.

Yantasee, W., G. E. Fryxell, et al. (2005b). "Nanostructured electrochemical sensors based on functionalized nanoporous silica for voltammetric analysis of lead, mercury, and copper." Journal of Nanoscience and Nanotechnology 5(9): 1537-1540.

Yoshitake, H., T. Yokoi, et al. (2002). "Adsorption of chromate and arsenate by amino-functionalized MCM-41 and SBA-1." Chemistry of Materials 14(11): 4603-4610.

Yoshitake, H. (2005). "Highly-controlled synthesis of organic layers on mesoporous silica: their structure and application to toxic ion adsorptions." New Journal of Chemistry 29: 1107-1117.

Zhang, L., W. Zhang, et al. (2003). "A new thioether functionalized organic-inorganic mesoporous composite as a highly selective and capacious Hg2+ adsorbent" Chemical Communications: 210-211.

Zhao, D., P. Yang, et al. (1998a). "Continuous mesoporous silica films with highly ordered large pore structures." Advanced Materials 10(16): 1380.

Zhao, D. Y., Q. S. Huo, et al. (1998b). "Nonionic triblock and star diblock copolymer and oligomeric surfactant syntheses of highly ordered, hydrothermally stable, mesoporous silica structures." Journal of the American Chemical Society 120(24): 6024-6036.

Zhao, D. Y., P. D. Yang, et al. (1998c). "Topological construction of mesoporous materials." Current Opinion in Solid State & Materials Science 3(1): 111-121.

The invention claimed is:

1. An optical sensor, comprising:
    a functionalized composite material that comprises a bulk silicate material, and that exhibits modulation of at least one optical property upon absorption of at least one analyte; and
    an optical component associated with the functionalized composite material that measures the modulation of the at least one optical property of the functionalized composite material;
    wherein modulation of the at least one optical property of the functionalized composite material is indicative of the presence of the analyte;
    where the bulk silicate material comprises:
    silsesquioxanes; or
    silsesquioxanes mixed together with or condensed at the same time with inorganic materials comprising silicates formed from a monomer selected from sodium ortho silicate $Na_4SiO_4$ (or $2Na_2OSiO_2$), sodium meta silicate $Na_2SiO_3$ (or $NaO_2OSiO_2$), sodium di silicate $Na_2Si_2O_5$ (or $Na_2O_2SiO_2$), and sodium tetra silicate $Na_2Si_4O_9$ (or $Na_2O_4SiO_2$), optionally combined with metal oxides, aluminosilicates, or a combination thereof;
    where the silsesquioxanes are of general structure M-R'-M or M-R'—(Y)$_n$—R'-M;
    where M is a polymerizable inorganic group such as a silica-based group such as $SiX_3$;
    X is OR" or Cl or Br or I;
    R" is an organic group such as $C_nH_{2n+1}$ or an aromatic group such as phenyl;
    R' is an organic spacer which may be an aliphatic group such as —(CH$_2$)$_n$— optionally having substituents on the alkyl chain or an unsaturated hydrocarbon of any type including alkenes, alkynes, or arenes of general formula —$C_nH_{(2n-2m)}$—;
    m and n are independently integers from 1 to 20; and
    Y is a group containing one or more heteroatom selected from S, N, O, P.

2. The optical sensor of claim 1, wherein the optical component is selected from the group consisting of tapered fiber, field access block, an optical component of a refractometer, an optical component of an ellipsometer, and long period grating.

3. The optical sensor of claim 1, wherein the optical component is a long period grating.

4. The optical sensor of claim 1, wherein the bulk silicate material is prepared by co-condensation between an inorganic silica precursor and (i) a silsesquioxane precursor selected from $X_3Si$—R'—$SiX_3$, or (ii) a siloxane terminated organic polymerizable group selected from $X_3Si$—R'—Z, where Z is a polymerizable organic group selected from acrylate and styrene.

5. The optical sensor of claim 1, wherein the bulk silicate material is a silsesquioxane of general structure M-R'-M, where M is $Si(OEt)_3$ or $Si(OMe)_3$ and R' is —(CH$_2$)$_2$— or —[CH$_2$—CH(CH$_3$)]— or —CH=CH— or —C$_6$H$_4$— or —C$_6$H$_4$—C$_6$H$_4$— or —(CH$_2$)$_3$—(S)$_4$—(CH$_2$)$_3$—, or a combination of these.

6. The optical sensor of claim 1, wherein the bulk silicate material is formed from a monomer selected from $Si(OR)_4$ where R is an aliphatic group ($C_nH_{2n+1}$), where n is an integer from 1 to 20.

7. The optical sensor of claim 6, wherein n is 1 or 2.

8. The optical sensor of claim 7, wherein the monomer is TEOS ($Si(OEt)_4$).

9. The optical sensor of claim 1, wherein the functionalized composite material comprises a functional group based on an element selected from S, N, O, F, C, H, P, and combinations thereof.

10. The optical sensor of claim 1, wherein the functionalized composite material comprises a substituted or unsubstituted functional group selected from SH, NH$_2$, PO(OH)$_2$, CO$_2$H, SR, NHR, PR$_3$, PO(OR)$_2$, NR$_2$, imidazole, benzimidazole, thiazole, POCH$_2$COR, crown ether, amide, a cyano-containing moiety, nitrile, isonitrile, sulfate, sulfonate, sulfone, sulfoxide, ester, thioester, dithioester, ether, halide, phosphate, phosphonate, phosphine, phosphite, isocyanourate, phosphonate ester, thiourea, urea, sulfide, disulfide, tetrasulfide, and combinations thereof.

11. The optical sensor of claim 1, wherein the functionalized composite material comprises a functional group selected from: an aromatic group selected from phenyl, naphthyl, and anthracyl; and a saturated or unsaturated aliphatic group.

12. The optical sensor of claim 1, wherein the analyte is selected from:
    inorganic species selected from mercury, cadmium, lead, copper, chromium, nickel, silver, gold, rhodium, ruthenium, palladium, platinum, boron, and arsenic and their compounds;
    organic species selected from chlorinated hydrocarbons, simple hydrocarbons of the formula $C_nH_{2n+2}$, where n is an integer from 1 to 20, and hydrocarbon blends;
    cyclic hydrocarbons and unsaturated hydrocarbons of the formula $C_nH_{2n-2m}$, where n and m are integers;
    aromatic hydrocarbons and polycyclic aromatic hydrocarbons (PAHs);
    and aromatic compounds functionalized by heteroatoms including functional groups of the elements N, O, S, P, Cl and Br, either within the ring or external to the aromatic ring; and
    gaseous analytes in all of the above classes.

13. The optical sensor of claim 1, wherein the at least one analyte is at least one metal or metal-containing compound.

14. The optical sensor of claim 13, wherein the at least one metal is mercury.

15. The optical sensor of claim 1, wherein the optical property is refractive index.

16. The optical sensor of claim 1, wherein the analyte is in a liquid medium.

17. The optical sensor of claim 1, wherein the analyte is in a gaseous medium.

18. The optical sensor of claim 13, wherein the at least one metal is lead or arsenic.

19. The optical sensor of claim 13, wherein the at least one metal is palladium.

20. The optical sensor of claim 13, wherein the at least one metal is platinum.

* * * * *